United States Patent
Yilmaz et al.

(10) Patent No.: US 9,334,171 B2
(45) Date of Patent: May 10, 2016

(54) ALKALI-FREE SYNTHESIS OF ZEOLITIC MATERIALS OF THE LEV-TYPE STRUCTURE

(75) Inventors: Bilge Yilmaz, Union, NJ (US); Ulrich Müller, Neustadt (DE); Meike Pfaff, Neunkirchen (DE); Hermann Gies, Sprockhövel (DE); Feng-Shou Xiao, Changchun (CN); Takashi Tatsumi, Kawasaki (JP); Xinhe Bao, Dalian (CN); Weiping Zhang, Dalian (CN); Dirk de Vos, Holsbeek (BE); Hiroyuki Imai, Tokyo (JP); Bin Xie, Chuangchun (CN); Haiyan Zhang, Chuangchun (CN)

(73) Assignees: BASF SE, Ludwigshafen (DE); TOKYO INSTITUTE OF TECHNOLOGY, Tokyo (JP)

( * ) Notice: Subject to any disclaimer, the term of this patent is extended or adjusted under 35 U.S.C. 154(b) by 242 days.

(21) Appl. No.: 13/163,377

(22) Filed: Jun. 17, 2011

(65) Prior Publication Data
US 2011/0312486 A1     Dec. 22, 2011

Related U.S. Application Data

(63) Continuation of application No. PCT/CN2010/074073, filed on Jun. 18, 2010, which is a continuation of application No. PCT/CN2010/078062, filed on Oct. 25, 2010.

(51) Int. Cl.
*C01B 39/48*       (2006.01)
*B01J 29/70*       (2006.01)
(Continued)

(52) U.S. Cl.
CPC ............... *C01B 39/46* (2013.01); *B01J 20/186* (2013.01); *B01J 20/2803* (2013.01);
(Continued)

(58) Field of Classification Search
CPC ........ C01B 39/48; B01J 29/70; B01J 2229/186
USPC .................................................. 423/700–718
See application file for complete search history.

(56) References Cited

U.S. PATENT DOCUMENTS 3,459,676 A * 8/1969 Kerr ................................ 502/68
4,372,930 A * 2/1983 Short et al. ..................... 423/706
(Continued)

FOREIGN PATENT DOCUMENTS

EP        91048 A1 * 10/1983 .............. C01B 33/28
EP        0107370         5/1984
(Continued)

OTHER PUBLICATIONS

De Luca, P. et al., Synthesis and Characterization of Al, B-levyne type crystals from gels containing methyl-quinuclidinium ions, 2004, Microporous and Mesoporous Materials, 71, pp. 39-49.*
(Continued)

*Primary Examiner* — David M Brunsman
(74) *Attorney, Agent, or Firm* — Servilla Whitney LLC

(57) ABSTRACT

A process for the production of a zeolitic material having an LEV-type framework structure comprising $YO_2$ and optionally comprising $X_2O_3$, wherein said process comprises preparing a mixture comprising one or more sources for $YO_2$, one or more solvents, and optionally comprising seed crystals; and crystallizing the mixture; wherein Y is a tetravalent element, and X is a trivalent element, and wherein the crystallized mixture contains 0.1 wt.-% or less, more preferably 0.01 wt.-% or less of one or more metals M based on 100 wt.-% of $YO_2$, wherein even more preferably the crystallized mixture contains no metal M, wherein M stands for sodium and/or potassium, wherein preferably M stands for the group of alkali and alkaline earth metals.

40 Claims, 3 Drawing Sheets

(51) Int. Cl.
  C01B 39/46    (2006.01)
  B01J 20/18    (2006.01)
  B01J 20/28    (2006.01)
  C07C 1/20     (2006.01)
  C10G 3/00     (2006.01)
  C10G 11/18    (2006.01)
  C10G 25/03    (2006.01)
  C01B 37/02    (2006.01)
  B01D 53/94    (2006.01)

(52) U.S. Cl.
  CPC ..... *B01J 20/28011* (2013.01); *B01J 20/28042* (2013.01); *B01J 20/28057* (2013.01); *B01J 29/70* (2013.01); *C01B 37/02* (2013.01); *C01B 39/48* (2013.01); *C07C 1/20* (2013.01); *C10G 3/49* (2013.01); *C10G 11/18* (2013.01); *C10G 25/03* (2013.01); *B01D 53/9418* (2013.01); *B01D 2251/2067* (2013.01); *B01D 2253/108* (2013.01); *B01D 2253/3425* (2013.01); *B01D 2255/20738* (2013.01); *B01D 2255/20761* (2013.01); *B01D 2255/50* (2013.01); *B01D 2255/9207* (2013.01); *B01D 2257/402* (2013.01); *B01D 2257/404* (2013.01); *B01D 2257/406* (2013.01); *B01D 2258/012* (2013.01); *B01J 2229/186* (2013.01); *C01P 2006/12* (2013.01); *C07C 2529/70* (2013.01); *C07C 2529/80* (2013.01); *C10G 2300/405* (2013.01); *C10G 2300/70* (2013.01); *Y02C 20/10* (2013.01); *Y02P 20/153* (2015.11); *Y02P 20/52* (2015.11)

(56) References Cited

U.S. PATENT DOCUMENTS

| | | | | |
|---|---|---|---|---|
| 4,495,303 | A * | 1/1985 | Kuehl | 502/62 |
| 5,334,367 | A * | 8/1994 | Rosinski et al. | 423/704 |
| 7,264,789 | B1 * | 9/2007 | Van Den Berge et al. | 423/716 |
| 2004/0215044 | A1 * | 10/2004 | Mertens et al. | 585/639 |
| 2005/0197520 | A1 * | 9/2005 | Mertens et al. | 585/640 |
| 2010/0092361 | A1 * | 4/2010 | Li et al. | 423/239.2 |
| 2011/0312486 | A1 * | 12/2011 | Yilmaz | B01J 20/186 502/60 |
| 2011/0313226 | A1 * | 12/2011 | Yilmaz | B01J 20/186 585/639 |
| 2013/0317269 | A1 * | 11/2013 | Nesterenko et al. | 585/329 |

FOREIGN PATENT DOCUMENTS

| WO | WO-2005/063624 | 7/2005 |
|---|---|---|
| WO | WO-2007/094949 | 8/2007 |

OTHER PUBLICATIONS

Yamamoto et al., "Synthesis and structure analysis of RUB-50, an LEV-type aluminosilicate zeolite", Microporous and Mesoporous materials, 128, 2010, pp. 150-157.*

Luca et al, "Synthesis and characterization of Al,B-levyne type crystals from gels containing methyl-quinuclidinium ions", Microporous and Mesoporous Materials, 71, 2004, pp. 39-49.*

PCT International Search Report in PCT/IB2011/052658, mailed Oct. 27, 2011, 5 pgs.

Caullet, P. et al., "Synthesis of LEV-type Zeolite from Aqueous Nonalkaline Fluoride Aluminosilicate Gels", *Zeolite*, vol. 5 1995, 139-147.

Yamamoto, Katsutoshi et al., "Synthesis and Structure Analysis of RUB-50, an LEV-Type Aluminosilicate Zeolite", *Microporous and Mesoporous Materials* 128 2010, 150-157.

"International Preliminary Report on Patentability", Oct. 25, 2012, pp. 1-7.

Extended European Search Report in EP11795287.9, dated Dec. 3, 2014, 9 pages.

Zhao, Zhenchao et al., "Insights into the Topotactic Conversion Process from Layered Silicate RUB-36 to FER-type Zeolite by Layer Reassembly", Chemistry of Materials, 2013, 25, pp. 840-847.

* cited by examiner

US 9,334,171 B2

ALKALI-FREE SYNTHESIS OF ZEOLITIC MATERIALS OF THE LEV-TYPE STRUCTURE

CROSS-REFERENCE TO RELATED APPLICATIONS

This application claims benefit under 35 USC 120 and 365(c) of PCT application PCT/CN/2010/074073, filed Jun. 18, 2010 and PCT Application PCT/CN/2010/078062, filed Oct. 25, 2010. The foregoing applications are hereby incorporated herein by reference in their entirety.

TECHNICAL FIELD

The present invention relates to a method for the production of a zeolitic material having an LEV-type framework structure wherein the reaction mixture to be crystallized contains very little to no sodium or potassium, and preferably contains very little to no alkali and alkaline earth metals. Furthermore, the present invention relates to a non-ion-exchanged zeolitic material having an LEV-type framework structure which contains very little to no sodium or potassium, and which preferably contains very little to no alkali and alkaline earth metals, as well as to the use of such zeolitic materials having an LEV-type framework structure.

BACKGROUND

The LEV-type framework is characterized by heptadecahedral cavities to which the LEV-type zeolites owe their large micropore volume, although this structure only has small eight-membered ring (8MR) pore openings. The framework density of Levyne is comparable to those of Chabazite (CHA) and Erionite (ERI) having closely related framework structures. Thus, although recent research efforts have focused on large or ultra-large pore zeolites having twelve MR or larger pore openings, small pore zeolites are still of importance because they exhibit zeolite-specific definite shape selectivity with respect to reactant molecules in catalyst applications. In particular, such small pore zeolites having large micropore volumes are attractive due to their large adsorption capacities.

Synthetic Levyne-type zeolites are typically prepared using exotic organotemplates as structure directing agents, such as quinuclidine-based templates, such that their synthesis typically involves high costs. A lower cost alternative is to use diethyldimethylammonium hydroxide as a structure directing agent wherein the diethyldimethylammonium cations act as the organotemplate. Thus, U.S. Pat. No. 7,264,789 B1 discloses a method for preparing LEV-type zeolites which alternatively uses choline and diethyldimethylammonium as organotemplate. A method for the preparation of the LEV-type zeolite RUB-50 using the diethyldimethylammonium cation as oraganotemplate is disclosed in Yamamoto et al. Micropor. Mesopor. Mater. 2010, Vol. 128, pp. 150-157.

Nevertheless, although some progress has been achieved regarding the costs of the organotemplate used in the synthesis of LEV-type zeolites, there remains a need for further improving the efficiency of the synthetic procedure which normally further involves both calcination and ion-exchange steps for obtaining the H-form of the aforementioned LEV-type zeoites. In particular, in addition to requiring the removal of the organotemplates used in synthesis by thermal treatment of the crystallization products in a calcination step, the product must furthermore be subject to an ion-exchange procedure for removing alkali metal ions, and in particular sodium or potassium present as counter-ions to the negatively charged framework structure in the zeolitic material for finally obtaining the commercially interesting H-form of the LEV-type zeolites. Said ion-exchange to the H-form is normally achieved by subjecting the calcined material to one or more ion-exchange steps with an ammonium salt, after which ammonia is removed by thermal treatment of the ion-exchanged product to finally obtain the H-form LEV-type zeolite.

Furthermore, the synthetic procedures of LEV-type zeolites typically afford nanocrystalline materials which require a relatively elaborate work-up procedure for their washing and isolation. Thus the washing and isolation procedures disclosed in Yamamoto et al. as well as in U.S. Pat. No. 7,264,789 B1 both involve centrifugation procedures coupled to intermediate washing steps for obtaining the crystallized material in a form in which it may then be further processed. In particular, the isolation methods of the nanocrystalline products require an exceptional handling using costly apparatus. More importantly, however, said requirements constitute an important obstacle to the production of LEV-type zeolites on an industrial scale due to the considerable difficulties of efficiently working up such materials in a large scale synthetic environment.

Consequently, in view of the above, it is apparent that the production LEV-type zeolitic materials remains a laborious enterprise which involves a time- and cost-intensive work-up, such that there remains a considerable need of providing an efficient procedure for their production. This applies in particular with respect to the prospect of efficiently producing LEV-type zeolitic materials on an industrial scale.

SUMMARY

The present invention includes the following embodiments, wherein these include the specific combinations of embodiments as indicated by the respective interdependencies defined therein:

1. A process for the production of a zeolitic material having an LEV-type framework structure comprising $YO_2$ and optionally comprising $X_2O_3$, wherein said process comprises the steps of
    (1) preparing a mixture comprising one or more sources for $YO_2$, one or more solvents, and optionally comprising seed crystals; and
    (2) crystallizing the mixture obtained in step (1);
    wherein Y is a tetravalent element, and X is a trivalent element, and
    wherein the mixture crystallized in step (2) contains 3 wt.-% or less of one or more metals M based on 100 wt.-% of $YO_2$, preferably 1 wt.-% or less, more preferably 0.5 wt.-% or less, more preferably 0.1 wt.-% or less, more preferably 0.05 wt.-% or less, more preferably 0.01 wt.-% or less, more preferably 0.005 wt.-% or less, more preferably 0.001 wt.-% or less, more preferably 0.0005 wt.-% or less, more preferably 0.0001 wt.-% or less of one or more metals M based on 100 wt.-% of $YO_2$, wherein even more preferably the mixture crystallized in step (2) contains no metal M,
    wherein M stands for sodium or potassium, preferably for sodium and potassium, more preferably for the group of alkali metals, wherein even more preferably M stands for the group of alkali and alkaline earth metals.
2. The process of embodiment 1, wherein the molar ratio of the total amount of the one or more solvents to $YO_2$ of the mixture obtained in step (1) is 50 or less, and preferably ranges from 0.5 to 30, more preferably from 1 to 20, more preferably from 2 to 15, more preferably from 3 to 10, more preferably from 3.5 to 8, more preferably from 4 to 6, and even more preferably from 4.5 to 5.5.

3. The process of embodiment 1 or 2, wherein the one or more solvents comprise one or more polar solvents, wherein the one or more polar solvents are preferably selected from the group consisting of alkanols, water, and mixtures of two or more thereof, more preferably from the group consisting of methanol, ethanol, n-propanol, iso-propanol, water, and mixtures of two or more thereof, more preferably from the group consisting of methanol, ethanol, water, and mixtures of two or more thereof, wherein even more preferably the one or more polar solvents comprise water, preferably distilled water.

4. The process of any of embodiments 1 to 3, wherein the mixture in step (1) further comprises one or more organotemplates, the one or more organotemplates preferably comprising one or more compounds selected from the group consisting of tetraalkylammonium compounds, 1-methyl-1-azonia-4-azabicyclo[2.2.2]octane, N-methylquinuclidinium compounds, choline compounds, and mixtures of two or more thereof, preferably one or more tetraalkylammonium compounds selected from the group consisting of diethyldimethylammonium compounds, triethylmethylammonium compounds, and mixtures of two or more thereof, wherein more preferably the one or more organotemplates comprises one or more diethyldimethylammonium compounds, more preferably one or more diethyldimethylammonium salts, wherein the one or more diethyldimethylammonium salts are preferably hydroxide and/or halide, wherein more preferably the salts are selected from the group consisting of hydroxide, chloride, bromide, and mixtures of two or more thereof, wherein even more preferably the one or more organotemplates comprises diethyldimethylammonium hydroxide and/or chloride, preferably diethyldimethylammonium hydroxide.

5. The process of any of embodiments 1 to 4, wherein the molar ratio of the total amount of the one or more organotemplates to $YO_2$ of the mixture obtained in step (1) ranges from 0.01 to 2, preferably from 0.05 to 1, more preferably from 0.1 to 0.8, more preferably from 0.3 to 0.7, more preferably from 0.4 to 0.6, and even more preferably from 0.45 to 0.55.

6. The process of any of embodiments 1 to 5, wherein Y is selected from the group consisting of Si, Sn, Ti, Zr, Ge, and mixtures of two or more thereof, Y preferably being Si.

7. The process of any of embodiments 1 to 6, wherein X is selected from the group consisting of Al, B, In, Ga, and mixtures of two or more thereof, X preferably being Al and/or B, and more preferably being Al.

8. The process of any of embodiments 1 to 7, wherein the one or more sources for $YO_2$ comprises silica, preferably fumed silica.

9. The process of any of embodiments 1 to 8, wherein the mixture in step (1) further comprises one or more sources for $X_2O_3$.

10. The process of embodiment 9, wherein the one or more sources for $X_2O_3$ comprises one or more aluminum compounds, preferably alumina and/or aluminum hydroxide, and even more preferably aluminum hydroxide.

11. The process of embodiment 9 or 10, wherein the $YO_2$:$X_2O_3$ molar ratio of the mixture obtained in step (1) ranges from 2 to 200, preferably from 5 to 150, more preferably from 10 to 100, more preferably from 15 to 80, and even more preferably from 20 to 60.

12. The process of any of embodiments 1 to 11, wherein the mixture according to step (1) further comprises one or more sources for $OH^-$, wherein said one or more sources for $OH^-$ preferably comprises a hydroxide of an organotemplate salt, more preferably one or more hydroxides selected from the group consisting of tetraalkylammonium hydroxides, 1-methyl-1-azonia-4-azabicyclo[2.2.2]octane hydroxide, N-methylquinuclidinium hydroxide, choline hydroxide, and mixtures of two or more thereof, preferably one or more tetraalkylammonium hydroxides, more preferably diethyldimethylammonium and/or triethylmethylammonium hydroxide, wherein even more preferably the one or more sources for $OH^-$ comprises diethyldimethylammonium hydroxide.

13. The process of embodiment 12, wherein the $OH^-$:$YO_2$ molar ratio of the mixture obtained in step (1) ranges from 0.01 to 5, preferably from 0.05 to 2, more preferably from 0.1 to 1.5, more preferably from 0.2 to 1, more preferably from 0.4 to 0.6, and even more preferably from 0.45 to 0.55.

14. The process of any of embodiments 1 to 13, wherein the mixture according to step (1) further comprises one or more sources of one or more elements suitable for isomorphous substitution of at least a portion of the Y atoms and/or of the X atoms in the LEV-type framework structure, wherein the one or more elements are preferably selected from the group consisting of B, Fe, Ti, Sn, Ga, Ge, Zr, V, Nb, Cu, Zn, Li, Be, and mixtures of two or more thereof, more preferably wherein the one or more elements are selected from the group consisting of B, Fe, Ti, Sn, Zr, Cu, and mixtures of two or more thereof, wherein even more preferably the one or more element is Ti and/or B, preferably Ti.

15. The process of embodiment 14, wherein the molar ratio of $YO_2$ to the total amount of the one or more elements suitable for isomorphous substitution of at least a portion of the Y atoms and/or of the X atoms in the LEV-type framework structure ranges from 3 to 300, preferably from 10 to 200, more preferably from 30 to 150, more preferably from 40 to 100, and even more preferably from 50 to 90.

16. The process of any of embodiments 4 to 15, wherein the molar ratio of $YO_2$ to $X_2O_3$ to the total amount of the one or more organotemplates of the mixture obtained in step (1) ranges from 1:(0.005-1):(0.05-10), preferably from 1:(0.01-0.5):(0.1-5), more preferably from 1:(0.012-0.2):(0.1-5), more preferably from 1:(0.015-0.1):(0.2-2), from 1:(0.018-0.07):(0.4-1), and even more preferably from 1:(0.02-0.05):(0.45-0.55).

17. The process of any of embodiments 1 to 16, wherein the crystallization in step (2) involves heating of the mixture, preferably at a temperature ranging from 50 to 250° C., more preferably from 80 to 200° C., more preferably from 100 to 180° C., more preferably from 120 to 170° C., more preferably from 140 to 160° C., and even more preferably from 145 to 155° C.

18. The process of embodiment 17, wherein the crystallization in step (2) is conducted under solvothermal conditions, preferably under hydrothermal conditions.

19. The process of any of embodiments 1 to 18, wherein the crystallization in step (2) involves heating of the mixture for at least 0.1 d, and preferably for a period ranging from 0.5 to 50 d, preferably from 1 to 30 d, more preferably from 1.5 to 13 d, more preferably from 2 to 10 d, more preferably from 2 to 7 d, more preferably from 2.5 to 5 d, and even more preferably from 2.5 to 3.5 d.

20. The process of any of embodiments 1 to 19, wherein the crystallization in step (2) involves agitating the mixture, preferably by stirring and/or rotation, more preferably by stirring of the mixture obtained in step (1).

21. The process of any of embodiments 1 to 20, further comprising one or more of the following steps of
   (3) isolating the zeolitic material having an LEV-type framework structure, preferably by filtration, ultrafiltration, diafiltration, centrifugation and/or decantation methods, and/or
   (4) washing the zeolitic material having an LEV-type framework structure, and/or
   (5) drying and/or calcining the zeolitic material having an LEV-type framework structure, and/or
   (6) subjecting the zeolitic material having an LEV-type framework structure to an ion-exchange procedure,
   wherein the steps (3) and/or (4) and/or (5) and/or (6) can be conducted in any order, and
   wherein one or more of said steps is preferably repeated one or more times.
22. The process of embodiment 21, wherein the calcination in step (5) is conducted at a temperature in the range of from 300 to 900° C., preferably from 400 to 800° C., more preferably from 500 to 700° C., and even more preferably from 550 to 650° C.
23. The process of embodiment 21 or 22, wherein after step (2) and prior to step (3) the pH of the crystallization product is adjusted to a pH in the range of from 5 to 12, preferably from 6 to 11, more preferably from 7 to 10, more preferably from 7.5 to 9, and even more preferably to a pH in the range of from 8 to 8.5.
24. The process of any of embodiments 21 to 23, wherein in step (6) the zeolitic material having an LEV-type framework is ion-exchanged with at least one cation and/or cationic element, wherein the at least one cation and/or cationic element is preferably selected from the group consisting of $H^+$, $NH_4^+$, Sr, Zr, Cr, Fe, Co, Ni, Cu, Zn, Ru, Rh, Pd, Ag, Os, Ir, Pt, Au, and mixtures of two or more thereof, more preferably from the group consisting of $H^+$, $NH_4^+$, Sr, Cr, Fe, Co, Ni, Cu, and mixtures of two or more thereof, and even more preferably from the group consisting of $H^+$, $NH_4^+$, Fe, Cu, and mixtures of two or more thereof.
25. The process of any of embodiments 1 to 24, wherein the zeolitic material having an LEV-type framework structure formed in step (2) comprises one or more zeolites selected from the group consisting of Levyne, LZ-132, NU-3, RUB-1, ZK-20, ZSM-45, RUB-50, and mixtures of two or more thereof, wherein preferably the zeolitic material comprises RUB-50.
26. The process of any of embodiments 1 to 25, wherein the seed crystals at least partially comprise zeolitic material not having an LEV-type framework structure, wherein preferably the seed crystals do not comprise zeolitic material having an LEV-type framework structure, wherein the zeolitic material not having an LEV-type framework material preferably comprises zeolitic material having a CHA-type framework structure.
27. The process of embodiment 26, wherein the zeolitic material having a CHA-type framework structure contained in the seed crystals comprises chabazite and/or SSZ-13, preferably SSZ-13.
28. The process of any of embodiments 1 to 25, wherein the seed crystals at least partially comprise zeolitic material having an LEV-type framework structure, wherein the zeolitic material having an LEV-type framework structure is preferably the zeolitic material obtained or obtainable according to any one of embodiments 1 to 28.
29. The process of embodiment 28, wherein the zeolitic material having an LEV-type framework structure contained in the seed crystals comprises one or more zeolites selected from the group consisting of Levyne, LZ-132, NU-3, RUB-1, ZK-20, ZSM-45, RUB-50, and mixtures of two or more thereof, wherein the seed crystals preferably comprise RUB-50.
30. The process of any of embodiments 1 to 29, wherein the amount of seed crystals in the mixture according to step (1) ranges from 0.01 to 30 wt.-% based on 100 wt.-% of $YO_2$ in the at least one source for $YO_2$, preferably from 0.1 to 20 wt.-%, more preferably from 0.5 to 10 wt.-%, more preferably from 2 to 8 wt.-%, and even more preferably from 3 to 5 wt.-% based on 100 wt.-% of $YO_2$.
31. The process of any of embodiments 1 to 29, wherein the mixture according to step (1) contains 5 wt.-% or less of seed crystals based on 100 wt.-% of $YO_2$, preferably 1 wt.-% or less, more preferably 0.5 wt.-% or less, more preferably 0.1 wt.-% or less, more preferably 0.01 wt.-% or less, and wherein even more preferably, the mixture according to step (1) contains no seed crystals.
32. A zeolitic material having an LEV-type framework structure obtainable and/or obtained according to the process of any one of embodiments 1 to 31, wherein the zeolitic material is preferably non-ion-exchanged.
33. A non-ion-exchanged zeolitic material, preferably obtainable and/or obtained according to the process of any one of embodiments 1 to 31, said zeolitic material having an LEV-type framework structure comprising $YO_2$ and optionally comprising $X_2O_3$,
   wherein Y is a tetravalent element, and X is a trivalent element,
   wherein the zeolitic material contains 3 wt.-% or less of one or more metals M based on 100 wt-% of X, preferably 3 wt.-% or less, more preferably 1 wt.-% or less, more preferably 0.5 wt.-% or less, more preferably 0.1 wt.-% or less, more preferably 0.05 wt.-% or less, more preferably 0.01 wt.-% or less, more preferably 0.005 wt.-% or less, more preferably 0.001 wt.-% or less, more preferably 0.0005 wt.-% or less, more preferably 0.0001 wt.-% or less of one or more metals M based on 100 wt.-% of X,
   wherein even more preferably the zeolitic material contains no metal M,
   wherein M stands for sodium or potassium, preferably for sodium and potassium, more preferably for the group of alkali metals, wherein even more preferably M stands for the group of alkali and alkaline earth metals.
34. The zeolitic material of embodiment 32 or 33, wherein the zeolitic material displays an Y:X atomic ratio of from 1 to 200, preferably from 1 to 100, more preferably from 2 to 50, more preferably from 5 to 30, more preferably from 7 to 20, more preferably from 8 to 15, and even more preferably from 9 to 14.
35. The zeolitic material of any of embodiments 32 to 34, wherein Y is selected from the group consisting of Si, Sn, Ti, Zr, Ge, and mixtures of two or more thereof, Y preferably being Si.
36. The zeolitic material of any of embodiments 32 to 35, wherein X is selected from the group consisting of Al, B, In, Ga, and mixtures of two or more thereof, X preferably being Al and/or B, and more preferably being Al.
37. The zeolitic material of any of embodiments 32 to 36, said material having an X-ray diffraction pattern comprising at least the following reflections:

| Intensity (%) | Diffraction angle 2θ/° [Cu K(alpha 1)] |
|---|---|
| [21-50] | [10.75-11.37] |
| [18-30] | [13.21-13.77] |
| [52-68] | [17.23-17.77] |
| [49-58] | [20.93-21.50] |
| 100 | [21.89-22.43] |
| [34-54] | [28.53-29.09] |
| [36-69] | [32.28-32.78] |
| [9-23] | [51.67-52.23] |
| [6-16] | [55.75-56.36] | wherein 100% relates to the intensity of the maximum peak in the X-ray powder diffraction pattern.

38. The zeolitic material of any of embodiments 32 to 37, wherein at least a portion of the Y atoms and/or of the X atoms in the LEV-type framework structure is isomorphously substituted by one or more elements, wherein the one or more elements are preferably selected from the group consisting of B, Fe, Ti, Sn, Ga, Ge, Zr, V, Nb, Cu, Zn, Li, Be, and mixtures of two or more thereof, more preferably wherein the one or more elements are selected from the group consisting of B, Fe, Ti, Sn, Zr, Cu, and mixtures of two or more thereof, wherein even more preferably the one or more element is Ti and/or B, preferably Ti.

39. The zeolitic material of embodiment 38, wherein the molar ratio of $YO_2$ to the total amount of the one or more elements by which the LEV-type framework structure is isomorphously substituted ranges from 5 to 100, preferably from 10 to 80, more preferably from 20 to 70, and even more preferably from 25 to 65.

40. The zeolitic material of any of embodiments 32 to 39, wherein said material comprises one or more zeolites selected from the group consisting of Levyne, LZ-132, NU-3, RUB-1, ZK-20, ZSM-45, RUB-50, and mixtures of two or more thereof, wherein preferably the zeolitic material comprises RUB-50.

41. The zeolitic material of any of embodiments 32 to 40, wherein the BET surface area of the zeolitic material determined according to DIN 66135 ranges from 650 to 1,100 m²/g, preferably from 750 to 1,050 m²/g, more preferably from 800 to 1,000 m²/g, more preferably from 820 to 900 m²/g, and even more preferably from 840 to 865 m²/g, wherein the zeolitic material is preferably a calcined zeolitic material.

42. Use of a zeolitic material of any of embodiments 32 to 41 as a molecular sieve, catalyst, catalyst support, and/or as an adsorbent, wherein the zeolitic material is preferably used as a molecular trap for chemical compounds, as a catalyst and/or as a catalyst support.

DETAILED DESCRIPTION

Figure 1:
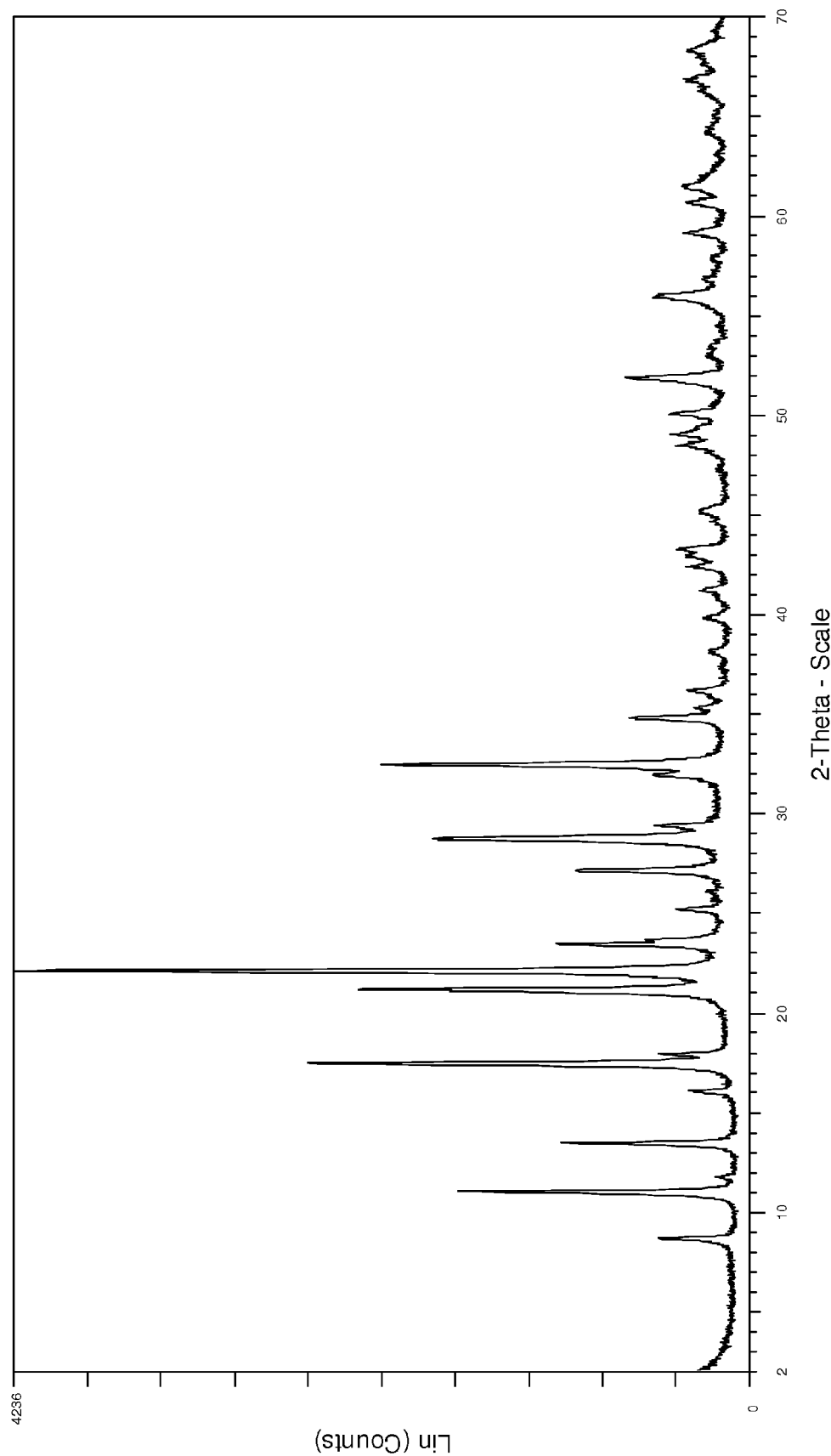
FIGS. 1 to 3 show the X-ray diffraction pattern of the crystalline material obtained according to Examples 1 to 3, respectively, wherein FIG. 3 further includes the line pattern of the aluminum fluoride silicate compound $Al_{5.4}Si_{48.6}F_{0.8}O_{108}$ having the LEV-type framework structure for comparison.

Embodiments of the present invention provide an improved process for the production of a zeolitic material having an LEV-type framework structure, in particular with respect to the production efficiency and/or with respect to the type of products which may be accessed by the production process. One or more embodiments provide an improved zeolitic material, in particular with respect to its potential applications including, for example, its use as a molecular trap for organic compounds and/or as a catalyst or also as a catalyst support.

Thus, embodiments of the present invention relates to a process for the production of a zeolitic material having an LEV-type framework structure comprising $YO_2$ and optionally comprising $X_2O_3$, wherein said process comprises:
(1) preparing a mixture comprising one or more sources for $YO_2$, one or more solvents, and optionally comprising seed crystals; and
(2) crystallizing the mixture obtained in step (1);
wherein Y is a tetravalent element, and X is a trivalent element, and
wherein the mixture crystallized in step (2) contains 3 wt.-% or less of one or more metals M based on 100 wt-% of $YO_2$, preferably 1 wt.-% or less, more preferably 0.5 wt.-% or less, more preferably 0.1 wt.-% or less, more preferably 0.05 wt.-% or less, more preferably 0.01 wt.-% or less, more preferably 0.005 wt.-% or less, more preferably 0.001 wt.-% or less, more preferably 0.0005 wt.-% or less, more preferably 0.0001 wt.-% or less of one or more metals M based on 100 wt.-% of $YO_2$, wherein even more preferably the mixture crystallized in step (2) contains no metal M, wherein M stands for sodium or potassium, preferably for sodium and potassium, more preferably for the group of alkali metals, wherein even more preferably M stands for the group of alkali and alkaline earth metals.

Within the meaning of embodiments of the present invention, the term "group of alkali metals" refers to the group of elements Li, Na, K, Rb, Cs, and Fr. Furthermore, the term "group of alkaline earth metals" refers to the group of elements Be, Mg, Ca, Sr, Ba, and Ra.

In particular, it has surprisingly been found that it is possible to crystallize a zeolitic material having an LEV-type framework structure from a mixture containing little to no sodium or potassium, and preferably little to no alkali and alkaline earth materials. Accordingly, a particularly advantageous process for the production of an LEV-type zeolitic material has been found wherein a product containing little to no sodium or potassium, and preferably little to no alkali and alkaline earth metals, may directly be obtained in a one-pot synthetic procedure. Consequently, the inventive procedure allows for the direct crystallization of a zeolitic material having an LEV-type framework which does not require an ion-exchange procedure for removing sodium or potassium, and preferably for removing any alkali and alkaline earth metals from the reaction product.

It is herewith noted that within the meaning of embodiments of the present invention, and in particular with respect to specific embodiments thereof, the term "comprising" is preferably used as meaning "consisting of". Furthermore, within the meaning of embodiments of the present invention, references to the molar content of $YO_2$ and $X_2O_3$ and to molar ratios thereof as contained in mixtures provided in the inventive process or in the zeolites described herein generally refer to the respective molar contents of Y and X on the basis of $YO_2$ and $X_2O_3$ as commonly employed in zeolite chemistry. In particular, references to $YO_2$ and $X_2O_3$ does not imply that said specific compounds must actually be contained in mixtures provided in the inventive process or in the zeolites, but rather refer to the molar amounts of Y and X present therein in terms of $YO_2$ and $X_2O_3$, respectively.

Furthermore, according to embodiments and preferred embodiments of the present invention, $YO_2$ and $X_2O_3$ are comprised in the LEV-type framework structure as structure building elements, as opposed to non-framework elements which can be present in the pores and cavities formed by the framework structure and typical for zeolitic materials in general.

According to embodiments of the inventive process, a zeolitic material having an LEV-type framework structure is crystallized in step (2). Said material comprises $YO_2$, wherein Y stands for any conceivable tetravalent element, Y standing for either one or several tetravalent elements. Preferred tetravalent elements according to the present invention include Si, Sn, Ti, Zr, and Ge, and combinations thereof. More preferably, Y stands for Si, Ti, or Zr, or any combination of said trivalent elements, even more preferably for Si and/or Sn. According to embodiments of the present invention, it is particularly preferred that Y stands for Si.

Thus, in principle, any conceivable zeolitic material having an LEV-type framework structure may be formed in step (2) of the inventive process, provided that it comprises $YO_2$ as a framework element, wherein Y stands for any conceivable tetravalent element. According to preferred embodiments of the inventive process wherein $YO_2$ comprises $SiO_2$, it is further preferred that the zeolitic material having an LEV-type framework structure formed in step (2) comprises one or more zeolites selected from the group consisting of Levyne, LZ-132, NU-3, RUB-1, ZK-20, ZSM-45, RUB-50, and mixtures of two or more thereof, wherein even more preferably the zeolitic material comprises RUB-50.

Furthermore, according to the process of embodiments of the present invention, one or more sources for $YO_2$ can be provided in step (1) in any conceivable form, provided that a zeolitic material having an LEV-type framework structure comprising $YO_2$ can be crystallized in step (2), and provided that the mixture crystallized in step (2) contains little to no metal M according to embodiments and preferred embodiments of the inventive process. Preferably, $YO_2$ is provided as such and/or as a compound which comprises $YO_2$ as a chemical moiety and/or as a compound which (partly or entirely) is chemically transformed to $YO_2$ during the inventive process. In preferred embodiments of the present invention, Y stands for Si or for a combination of Si with one or more further tetravalent elements. The source for $SiO_2$ preferably provided in step (1) can be any conceivable source, provided that the mixture crystallized in step (2) contains little to no metal M according to embodiments and preferred embodiments of the inventive process.

In this respect, it is noted herewith that within the meaning of embodiments of the present invention, the terms "little to no" as used in the present description regarding the amount of the one or more metals M contained in the mixture crystallized in step (2) refers to an amount of 3 wt.-% or less of said one or more metals M based on 100 wt-% of $YO_2$, and preferably to 1 wt.-% or less thereof, more preferably 0.5 wt.-% or less, more preferably 0.1 wt.-% or less, more preferably 0.05 wt.-% or less, more preferably 0.01 wt.-% or less, more preferably 0.005 wt.-% or less, more preferably 0.001 wt.-% or less, more preferably 0.0005 wt.-% or less, and more preferably 0.0001 wt.-% or less of said one or more metals M based on 100 wt.-% of $YO_2$, wherein even more preferably the terms "little to no" indicate that the mixture crystallized in step (2) contains no metal M.

Thus, according to preferred embodiments of the inventive process, $YO_2$ is provided as such and/or as a compound which comprises $YO_2$ as a chemical moiety and/or as a compound which (partly or entirely) is chemically transformed to $YO_2$ during the inventive process. According to particularly preferred embodiments wherein Y stands for Si or for a combination of Si with one or more further tetravalent elements, there can therefore be used, for example, all types of silica and silicates, preferably fumed silica, silica hydrosols, reactive amorphous solid silicas, silica gel, silicic acid, metasilicate hydrates, sesquisilicates or disilicates, colloidal silica, pyrogenic silica, silicic acid esters, or tetraalkoxysilanes, or mixtures of at least two of these compounds.

In preferred embodiments of the inventive process, wherein the mixture according to step (1) comprises at least one source for $SiO_2$, said source preferably comprises at least one compound selected from the group consisting of silica and silicates. Among the silica which may be employed, fumed silica is particularly preferred. According to particularly preferred embodiments the at least one source for $SiO_2$ comprises silica, preferably fumed silica.

Further preferred are embodiments wherein the zeolitic material having an LEV-type framework structure further comprises $X_2O_3$, wherein X stands for any conceivable trivalent element, X standing for either one or several trivalent elements. Preferred tetravalent elements according to the present invention include Al, B, In, and Ga, and combinations thereof. More preferably, Y stands for Al, B, or In, or any combination of said trivalent elements, even more preferably for Al and/or B. According to embodiments of the present invention, it is particularly preferred that X stands for Al.

According to preferred embodiments of the present invention, wherein the zeolitic material having an LEV-type framework structure comprises $X_2O_3$, one or more sources for $X_2O_3$ are provided in step (1). In general, $X_2O_3$ can be provided in any conceivable form, provided that a zeolitic material having an LEV-type framework structure comprising $X_2O_3$ can be crystallized in step (2). Preferably, $X_2O_3$ is provided as such and/or as a compound which comprises $X_2O_3$ as a chemical moiety and/or as a compound which (partly or entirely) is chemically transformed to $X_2O_3$ during the inventive process.

In more preferred embodiments of the present invention, wherein X stands for Al or for a combination of Al with one or more further trivalent elements, the one or more sources for $Al_2O_3$ preferably provided in step (1) can be selected from any conceivable source, provided that the mixture crystallized in step (2) contains little to no metal M according to embodiments and preferred embodiments of the inventive process. There can be used for example any type of alumina; aluminate salts; aluminum alcoholates, such as, for example, aluminum triisopropylate; at least partially hydrated alumina such as, for example, AlO(OH), and aluminum hydroxide; as well as mixtures of two or more of any of the aforementioned examples for sources of $Al_2O_3$. Preferably, the one or more sources for $Al_2O_3$ comprises one or more aluminum alcoholates and/or one or more at least partially hydrated aluminas, more preferably one or more at least partially hydrated aluminas, wherein even more preferably the one or more sources for $Al_2O_3$ comprises aluminum hydroxide, and in particular $Al(OH)_3$.

In embodiments wherein X stands for B or for a combination of B with one or more trivalent elements and preferably Al, the one or more sources for $B_2O_3$ provided in step (1) may also be selected from practically any conceivable source. Examples thereof include free boric acid, borates, and boric esters such as, for example, triethyl borate or trimethyl borate, in addition to combinations of two or more thereof.

According to particularly preferred embodiments of the inventive process, the mixture according to step (1) comprises at least one silica as a source for $YO_2$ and at least one at least partially hydrated alumina as a source for $X_2O_3$, and more preferably at least one fumed silica and/or at least one of AlO(OH) and/or Al(OH)$_3$, wherein even more preferably the mixture according to (1) comprises at least one fumed silica and Al(OH)$_3$.

In preferred embodiments of the inventive process wherein the mixture obtained in step (1) comprises at least one source for X$_2$O$_3$, the YO$_2$:X$_2$O$_3$ molar ratio of the mixture can have any conceivable value, provided that a zeolitic material having an LEV-type framework structure comprising both YO$_2$ and X$_2$O$_3$ is crystallized in step (2). Generally, the molar ratio may range anywhere from 2 to 200, and preferably from 5 to 150, more preferably from 10 to 100, more preferably from 15 to 80, and even more preferably from 20 to 60.

According to the process of embodiments of the present invention, the mixture provided in step (1) can contain one or more sources for hydroxide anions OH$^-$. In general any conceivable source for OH$^-$ can be used, provided that the mixture crystallized in step (2) contains little to no metal M according to embodiments and preferred embodiments of the inventive process. Within a preferred meaning of the present invention, the term "source for OH$^-$" refers to chemical compounds and compositions which may be solvated in the one or more solvents provided in step (1) of the inventive process thus leading to the formation of at least partially solvated hydroxide ions and/or wherein hydroxide ions may be generated and dissociated from said one or more sources for OH$^-$ in the course of the inventive process, including in the course of the crystallization procedure in step (2).

According to particularly preferred embodiments of the inventive process, said one or more sources for OH$^-$ preferably comprises a hydroxide of an organotemplate salt which, according to further preferred embodiments of the present invention described below, may be comprised in the mixture in step (1). In principle, according to said preferred embodiments, one or more of any conceivable hydroxide salt of an organotemplate compound may be used as a source for OH$^-$, provided that a zeolitic material having an LEV-type framework structure may be formed in step (2), wherein more preferably one or more hydroxides selected from the group consisting of tetraalkylammonium hydroxides, 1-methyl-1-azonia-4-azabicyclo[2.2.2]octane hydroxide, N-methylquinuclidinium hydroxide, choline hydroxide, and mixtures of two or more thereof are comprised among the one or more sources for OH$^-$, more preferably one or more tetraalkylammonium hydroxides, more preferably diethyldimethylammonium and/or triethylmethylammonium hydroxide, wherein even more preferably the one or more sources for OH$^-$ comprises diethyldimethylammonium hydroxide In general the OH$^-$:YO$_2$ molar ratio of the mixture obtained in step (1) of the inventive process can have any conceivable value, provided that a zeolitic material having an LEV-type framework structure is crystallized in step (2). Preferably, the OH$^-$:YO$_2$ molar ratio ranges from 0.01 to 5, preferably from 0.05 to 2, more preferably from 0.1 to 1.5, more preferably from 0.2 to 1, more preferably from 0.4 to 0.6, and even more preferably from 0.45 to 0.55.

According to preferred embodiments of the inventive process, seed crystals are provided in step (1). In general, any conceivable seed crystals or mixtures thereof may be provided therein, provided that a zeolitic material having an LEV-type framework structure comprising YO$_2$ and optionally comprising X$_2$O$_3$ may be obtained in step (2).

According to certain preferred embodiments of the inventive process, the seed crystals provided in step (1) at least partially comprise zeolitic material having an LEV-type framework structure. In general, said seed crystals can comprise any zeolitic material having an LEV-type framework structure, provided that a zeolitic material having an LEV-type framework structure is crystallized in step (2). Preferably, the zeolitic material having an LEV-type framework structure comprised in the seed crystals is a zeolitic material obtained according to the inventive process. More preferably, the zeolitic material having an LEV-type framework structure comprised in the seed crystals is the same as the zeolitic material having an LEV-type framework structure which is then crystallized in step (2). Particularly preferred according to embodiments of the present invention are seed crystals comprising one or more zeolites selected from the group consisting of Levyne, LZ-132, NU-3, RUB-1, ZK-20, ZSM-45, RUB-50, and mixtures of two or more thereof, wherein even more preferably the seed crystals preferably comprise RUB-50. According to an even more preferred embodiment the seed crystals comprise one or more zeolites selected from the group consisting of Levyne, LZ-132, NU-3, RUB-1, ZK-20, ZSM-45, RUB-50, and mixtures of two or more thereof, wherein said one or more zeolites have been obtained according to the inventive process, wherein even more preferably RUB-50 obtained according to the inventive process is comprised in the seed crystals.

According to alternatively preferred embodiments of the inventive process, the seed crystals provided in step (1) at least partially comprise zeolitic material not having an LEV-type framework structure, wherein preferably the seed crystals do not comprise zeolitic material having an LEV-type framework structure. In general, said seed crystals can comprise any zeolitic material other than zeolitic materials having an LEV-type framework structure, provided that a zeolitic material having an LEV-type framework structure may be obtained in step (2). Thus, according to a further aspect of embodiments of the present invention, it has quite surprisingly been found that it is possible to produce a zeolitic material having an LEV-type framework structure using seed crystals not displaying the LEV-type framework structure of the zeolitic material obtained in step (2). This result was not only completely unexpected, but also provides considerable advantages since the general advantages linked to the use of a seeding material and, in particular to the use of seed crystals, may be achieved using heteroseeds which may be far easier to obtain and/or to manufacture, as a result of which the cost-effectiveness of the inventive process may be yet improved. According to a particularly preferred embodiment of the inventive process which employs seed crystals which at least in part do not comprise zeolitic material having an LEV-type framework structure, and which preferably do not comprise zeolitic material having an LEV-type framework structure, the seed crystals employed in said particularly preferred embodiments preferably comprise zeolitic material having a CHA-type framework structure, wherein more preferably the zeolitic material having a CHA-type framework structure contained in the seed crystals comprises chabazite and/or SSZ-13, and even more preferably SSZ-13.

According to the inventive process, any suitable amount of seed crystals can be optionally provided in the mixture according to step (1), provided that a zeolitic material having an LEV-type framework structure is crystallized in step (2). According to a preferred embodiment, the amount of seed crystals contained in the mixture according to step (1) ranges from 0.01 to 30 wt.-% based on 100 wt.-% of YO$_2$ in the at least one source for YO$_2$, and preferably from 0.1 to 20 wt.-%, more preferably from 0.5 to 10 wt.-%, more preferably from 2 to 8 wt.-%, and even more preferably from 3 to 5 wt.-% based on 100 wt.-% of YO$_2$. According to an alternatively preferred embodiment of the inventive process, the mixture according to step (1) contains 5 wt.-% or less of seed crystals based on 100 wt.-% of YO$_2$, preferably 1 wt.-% or less, more preferably 0.5 wt.-% or less, more preferably 0.1 wt.-% or less, more preferably 0.01 wt.-% or less, and wherein even more preferably, the mixture according to step (1) contains no seed crystals.

In step (1) according to embodiments of the present invention, the mixture can be prepared by any conceivable means, wherein mixing by agitation is preferred, preferably by means of stirring.

According to embodiments of the present invention, the mixture obtained in step (1) of the inventive process further comprises one or more solvents. In principle any conceivable solvents may be used, provided that a zeolitic material having an LEV-type framework structure can be crystallized in step (2). According to preferred embodiments, the one or more solvents comprise one or more polar solvents. In general, any polar solvent may be used including protic and aprotic solvents as well as combinations thereof, wherein solvents or solvent mixtures are preferably used which comprise one or more protic solvents. In particular it is preferred that the one or more solvents comprise one or more polar solvents selected from the group consisting of alkanols, water, and mixtures of two or more thereof, more preferably from the group consisting of methanol, ethanol, n-propanol, iso-propanol, water, and mixtures of two or more thereof, more preferably from the group consisting of methanol, ethanol, water, and mixtures of two or more thereof, wherein even more preferably the one or more polar solvents comprise water, and preferably distilled water.

Furthermore, the molar ratio of the total amount of the one or more solvents to the total amount of the one or more sources for $YO_2$ based on $YO_2$ as provided in step (1) is 9.5 or less, and is preferably comprised in the range of from 0.5 to 9, more preferably of from 1 to 8.5, more preferably of from 2 to 8, more preferably of from 3 to 7, more preferably of from 4 to 6, and wherein even more preferably the molar ratio of the total amount of the one or more solvents to the total amount of the one or more sources for $YO_2$ based on $YO_2$ is comprised in the range of from 4.5 to 5.5.

According to the inventive process, the mixture provided in step (1) may contain any further compound or material which may suitably be used for the crystallization of a zeolitic material having an LEV-type framework structure in step (2). In particular, according to preferred embodiments of the present invention, the mixture in step (1) further comprises one or more organotemplates which may suitable serve as structure directing agents in the crystallization process. In general, any structure directing agent and, in particular, any organotemplate may be used in the present invention, provided that a zeolitic material having an LEV-type framework structure may be obtained. According to the inventive process, it is preferred that the one or more organotemplates comprise one or more compounds selected from the group consisting of tetraalkylammonium compounds, 1-methyl-1-azonia-4-azabicyclo[2.2.2]octane, N-methylquinuclidinium compounds, choline compounds, and mixtures of two or more thereof, wherein preferably the one or more tetraalkylammonium compounds are selected from the group consisting of diethyldimethylammonium compounds, triethylmethylammonium compounds, and mixtures of two or more thereof. More preferably, the one or more organotemplates comprise one or more diethyldimethylammonium compounds, more preferably one or more diethyldimethylammonium salts. In principle, any diethyldimethylammonium salt may be used, wherein preferably diethyldimethylammonium hydroxide and/or one or more diethyldimethylammonium halides are used, more preferably the one or more diethyldimethylammonium salts selected from the group consisting of hydroxide, chloride, bromide, and mixtures of two or more thereof, wherein even more preferably the one or more organotemplates comprise diethyldimethylammonium hydroxide and/or chloride, and preferably diethyldimethylammonium hydroxide.

With respect to preferred embodiments of the present invention wherein the mixture in step (1) comprises one or more organotemplates, suitably as structure directing agents, there is no particular restriction as to the total amount of organotemplates which may be used, provided that a zeolitic material having an LEV-type framework structure according to the embodiments and preferred embodiments of the present invention may be obtained. Thus, by way of example, the molar ratio of the total amount of the one or more organotemplates to $YO_2$ of the mixture obtained in step (1) may range anywhere from 0.01 to 2, wherein preferably the total amount of the one or more organotemplates used ranges from 0.05 to 1, more preferably from 0.1 to 0.8, more preferably from 0.3 to 0.7, more preferably from 0.4 to 0.6, and even more preferably from 0.45 to 0.55.

Furthermore, it is particularly preferred according to the present invention that the mixture according to step (1) comprises one or more sources for $X_2O_3$ in addition to one or more organotemplates. According to said particularly preferred embodiments, any conceivable amounts of these components can be contained in the mixture provided that a zeolitic material having an LEV-type framework structure is crystallized in step (2), and the mixture crystallized in step (2) contains little to no metal M according to embodiments and preferred embodiments of the inventive process. Preferably, the molar ratio of $YO_2$ to $X_2O_3$ to the total amount of the one or more organotemplates of the mixture obtained in step (1) ranges from 1:(0.005-1):(0.05-10), preferably from 1:(0.01-0.5):(0.1-5), more preferably from 1:(0.012-0.2):(0.1-5), more preferably from 1:(0.015-0.1):(0.2-2), from 1:(0.018-0.07):(0.4-1), and even more preferably from 1:(0.02-0.05):(0.45-0.55).

Furthermore, according preferred embodiments of the inventive process, the mixture according to step (1) comprises one or more sources of one or more elements suitable for isomorphous substitution of at least a portion of the Y atoms and/or of the X atoms in the LEV-type framework structure. In general, any conceivable elements can be used provided that they may effectively be substituted into the LEV-type framework structure via isomorphous substitution. In preferred embodiments, the one or more elements are selected from the group consisting of B, Fe, Ti, Sn, Ga, Ge, Zr, V, Nb, Cu, Zn, Li, Be, and mixtures of two or more thereof, more preferably wherein the one or more elements are selected from the group consisting of B, Fe, Ti, Sn, Zr, Cu, and mixtures of two or more thereof, wherein even more preferably the one or more element is Ti and/or B, preferably Ti. According to further embodiments of the present invention which are particularly preferred, the one or more elements comprise Cu, wherein it is particularly preferred that the one or more element suitable for isomorphous substitution is Cu. According to yet further embodiments of the present invention which are particularly preferred, the one or more elements comprise Fe, wherein it is particularly preferred that the one or more element suitable for isomorphous substitution is Fe.

Therefore, embodiments of the present invention therefore also provide a one-pot synthetic procedure for the preparation of a zeolitic material having an LEV-type framework structure which is isomorphously substituted, wherein isomorphous substitution is not achieved by conventional processes involving the post-synthetic treatment of an existing framework, wherein framework elements are treated such that they may be replaced with other atoms which are then contained in the resulting framework structure. In particular, according to the inventive process it is not necessary to remove existing framework atoms for producing an isomorphously substituted framework structure.

Consequently, embodiments of the present invention also relate to a one-pot synthetic procedure for the production of a zeolitic material having an LEV-type framework structure, wherein at least a portion of the Y atoms and/or of the X atoms in the LEV-type framework structure is isomorphously substituted by one or more elements, wherein the one or more elements are preferably selected from the group consisting of B, Fe, Ti, Sn, Ga, Ge, Zr, V, Nb, Cu, Zn, Li, Be, and mixtures of two or more thereof, more preferably wherein the one or more elements are selected from the group consisting of B, Fe, Ti, Sn, Zr, Cu, and mixtures of two or more thereof, wherein even more preferably the one or more element is Ti and/or B, preferably Ti, wherein according to embodiments which are further preferred the one or more elements used for isomorphous substitution is Cu and/or Fe.

In general, according to step (1) of the inventive process, the molar ratio of $YO_2$ to the element or to the sum of the one or more elements suitable for isomorphous substitution can have any conceivable value, wherein the molar ratio preferably ranges from 3 to 300, preferably from 10 to 200, more preferably from 30 to 150, more preferably from 40 to 100, and even more preferably from 50 to 90.

In general, step (2) according to the inventive process can be conducted in any conceivable manner, provided that a zeolitic material having an LEV-type framework structure is crystallized from the mixture according to step (1). The mixture can be crystallized in any suitable type of vessel or receptacle, wherein a means of agitation is preferably employed, preferably by rotation of the vessel and/or stirring, and more preferably by stirring the mixture.

According to the inventive process, the mixture is preferably heated during at least a portion of the crystallization process in step (2). In general, the mixture can be heated to any conceivable temperature of crystallization, provided that a zeolitic material having an LEV-type framework structure is crystallized from the mixture. Thus, by way of example, the mixture may be heated in step (2) to a temperature comprised in the range of from 50 to 250° C., wherein preferably the mixture is heated in step (2) to a temperature of crystallization ranging from 80 to 200° C., more preferably from 100 to 180° C., more preferably from 120 to 170° C., more preferably from 140 to 160° C., and even more preferably from 145 to 155° C.

In preferred embodiments of the present invention, the mixture according to step (1) is subjected in step (2) to a pressure which is elevated with regard to normal pressure. The term "normal pressure" as used in the context of the present invention relates to a pressure of 101,325 Pa in the ideal case. However, this pressure may vary within boundaries known to the person skilled in the art. By way of example, this pressure can be in the range of from 95,000 to 106,000 or of from 96,000 to 105,000 or of from 97,000 to 104,000 or of from 98,000 to 103,000 or of from 99,000 to 102,000 Pa.

In preferred embodiments of the inventive process wherein a solvent is present in the mixture according to step (1), it is furthermore preferred that heating in step (2) is conducted under solvothermal conditions, meaning that the mixture is crystallized under autogenous pressure of the solvent which is used, for example by conducting heating in an autoclave or other crystallization vessel suited for generating solvothermal conditions. In particularly preferred embodiments wherein the solvent comprises water, preferably distilled water, heating in step (2) is accordingly preferably conducted under hydrothermal conditions.

The apparatus which can be used in the present invention for crystallization is not particularly restricted, provided that the desired parameters for the crystallization process can be realized, in particular with respect to the preferred embodiments requiring particular crystallization conditions. In the preferred embodiments conducted under solvothermal conditions, any type of autoclave or digestion vessel can be used, wherein a Teflon-lined apparatus is preferred.

In general, the duration of the crystallization process in step (2) of the inventive process is not particularly limited. Thus, the crystallization process may be conducted for any conceivable duration, provided that a zeolitic material having an LEV-type framework structure according to embodiments and preferred embodiments of the present invention is provided. Accordingly, in principle, the crystallization may be conducted for at least 0.1 d, wherein the mixture is preferably heated. In further preferred embodiments involving heating of the mixture obtained in step (1), said crystallization process is preferably conducted for a period ranging from 0.5 to 50 d, more preferably from 1 to 30 d, more preferably from 1.5 to 13 d, more preferably from 2 to 10 d, more preferably from 2 to 7 d, more preferably from 2.5 to 5 d, and even more preferably from 2.5 to 3.5 d.

According to preferred embodiments of the present invention, wherein the mixture is heated in step (2), said heating may be conducted during the entire crystallization process or during only one or more portions thereof, provided that a zeolitic material having the LEV-type framework structure is crystallized. Preferably, heating is conducted during the entire duration of crystallization.

In general, the process of embodiments of the present invention can optionally comprise further steps for the work-up and/or further physical and/or chemical transformation of the zeolitic material having an LEV-type framework structure crystallized in step (2) from the mixture provided in step (1). The crystallized material can for example be subject to any sequence of isolation (3) and/or washing procedures (4), wherein the zeolitic material obtained from crystallization in step (2) is preferably subject to at least one isolation (3) and at least one washing procedure (4).

Isolation of the crystallized product can be achieved by any conceivable means. Preferably, isolation of the crystallized product can be achieved by means of filtration, ultrafiltration, diafiltration, centrifugation and/or decantation methods, wherein filtration methods can involve suction and/or pressure filtration steps. Furthermore, for ease of isolation, any suitable compounds or compositions and in particular any suitable flocculating agent may be added and/or any suitable treatment may be performed to the zeolitic material obtained from crystallization in step (2) for facilitating the isolation procedure.

According to particularly preferred embodiments of the inventive process, after step (2) and prior to isolating (3) and/or washing (4) and/or drying (5) the zeolitic material having an LEV-type framework structure, preferably prior to isolating and/or washing, and even more preferably prior to isolating the zeolitic material, the pH of the crystallization product and in particular of the zeolitic material is adjusted to a pH in the range of from 5 to 12, preferably from 6 to 11, more preferably from 7 to 10, more preferably from 8 to 9.5, and even more preferably to a pH in the range of from 8.3 to 9.3. Thus, it has surprisingly been found that when adjusting the pH of the crystallization product and in particular of the zeolitic material having an LEV-type framework structure, the ease of isolating (3) and/or washing (4) the zeolitic material is greatly improved. In particular, the zeolitic material of which the pH has been adjusted accordingly may be easily filtered off and/or washed, and does not necessitate elaborate isolation and/or washing techniques involving for example ultrafiltration, diafiltration, and/or centrifugation, or combinations thereof, for isolation (3) and/or washing (4) thereof. These advantages have a particular impact on production methods conducted on a large scale and in particular on an industrial scale, since filtration means commonly used one this scale may be used in a highly efficient manner.

Furthermore and quite unexpectedly it has been found that when adjusting the pH of the crystallization product, and in particular in embodiments wherein adjusting the pH involves the lowering thereof towards by appropriate acidification, the Y:X atomic ratio of the crystallization product does not increase but rather remains practically constant or even increases. This applies in particular with respect to preferred embodiments of the present invention wherein Y comprises Si and X comprises Al. This finding is particularly surprising since the acidification of a aluminosilicate containing zeolitic material having an LEV-type framework structure is normally known to lead to the opposite effect as the one observed in the present invention, i.e. to an increase in the Si:Al atomic ratio and thus to a dealumination of the zeolitic material. Consequently, it has not only surprisingly been found that by adjusting the pH of the crystallization product the ease of isolation of the zeolitic material having an LEV-type framework structure may be greatly improved, but also that said adjustment of the pH level does not lead to an increase in the X:Y atomic ratio of the crystallization product, and in particular in the Si:Al atomic ratio of preferred embodiments.

With respect to one or more optional washing procedures, any conceivable solvent can be used. Washing agents which may be used are, for example, water, alcohols, such as methanol, ethanol or propanol, or mixtures of two or more thereof. Examples of mixtures are mixtures of two or more alcohols, such as methanol and ethanol or methanol and propanol or ethanol and propanol or methanol and ethanol and propanol, or mixtures of water and at least one alcohol, such as water and methanol or water and ethanol or water and propanol or water and methanol and ethanol or water and methanol and propanol or water and ethanol and propanol or water and methanol and ethanol and propanol. Water or a mixture of water and at least one alcohol, preferably water and ethanol, is preferred, distilled water being very particularly preferred as the only washing agent.

Preferably, the separated zeolitic material is washed until the pH of the washing agent, preferably the washwater, is in the range of from 6 to 8, preferably from 6.5 to 7.5, as determined via a standard glass electrode. According to embodiments which are further preferred, the separated zeolitic material is washed until the washing solvent or solvent mixture which is preferably water and more preferably distilled water displays a conductivity of 1000 $\mu S/cm^3$ or less, more preferably of 500 $\mu S/cm^3$ or less, more preferably of 200 $\mu S/cm^3$ or less, more preferably of 100 $\mu S/cm^3$ or less, and even more preferably of 50 $\mu S/cm^3$ or less.

Furthermore, the inventive process can optionally comprise one or more drying steps (5). In general, any conceivable means of drying can be used. Drying procedures preferably include heating and/or applying vacuum to the zeolitic material having an LEV-type framework structure. In alternatively preferred embodiments of the present invention, one or more drying steps may involve spray drying, and preferably spray granulation of the zeolitic material.

In embodiments which comprise at least one drying step (5), the drying temperatures are preferably in the range of from 25° C. to 150° C., more preferably of from 60 to 140° C., more preferably of from 70 to 130° C. and even more preferably in the range of from 75 to 125° C. The durations of drying are preferably in the range of from 2 to 60 h, more preferably in the range of 6 to 48 hours, and even more preferably of from 12 to 24 h.

Furthermore, in addition to or alternatively to at least one drying step, the inventive process preferably includes a calcination procedure which is preferably conducted after a step of drying the zeolitic material having an LEV-type framework structure. In principle, there is no particular restriction according to the present invention as to the temperature used for the preferred calcinations step, nor with respect to the duration thereof. Thus, by way of example, the calcination may be performed at a temperature ranging anywhere from 300 to 900° C., wherein it preferred that the calcinations be performed at a temperature comprised in the range of from 400 to 800° C., more preferably from 500 to 700° C., and even more preferably from 550 to 650° C. Furthermore, by way of example, the calcination may suitably be performed for a duration of from 1 to 48 h, wherein calcination is preferably performed for a duration of from 2 to 36 h, more preferably of from 4 to 24 h, more preferably of from 6 to 20 h, more preferably of from 8 to 12 h, and even more preferably of from 9 to 11.

According to the inventive process, the zeolitic material crystallized in step (2) can optionally be subject to at least one step of an ion-exchange procedure (6), wherein the term "ion-exchange" according to embodiments of the present invention generally refers to the exchange of non-framework ionic elements and/or molecules contained in the zeolitic material against suitable ionic elements and/or molecules, and preferably against suitable ionic elements.

In general, any conceivable ion-exchange procedure with one or more suitable ionic elements and/or molecules can be conducted on the zeolitic material. Preferably, as ionic elements at least one cation and/or cationic element is employed which is preferably selected from the group consisting of $H^+$, $NH_4^+$, Sr, Zr, Cr, Fe, Co, Ni, Cu, Zn, Ru, Rh, Pd, Ag, Os, Ir, Pt, Au, and mixtures of two or more thereof, more preferably from the group consisting of $H^+$, $NH_4^+$, Sr, Cr, Fe, Co, Ni, Cu, and mixtures of two or more thereof, and even more preferably from the group consisting of $H^+$, $NH_4^+$, Fe, Cu, and mixtures of two or more thereof. According to further preferred embodiments, the at least one cation and/or cationic element is preferably selected from the group consisting Sr, Zr, Cr, Fe, Co, Ni, Cu, Zn, Ru, Rh, Pd, Ag, Os, Ir, Pt, Au, and mixtures of two or more thereof, more preferably from the group consisting of Sr, Cr, Fe, Co, Ni, Cu, and mixtures of two or more thereof, wherein even more preferably the at least one cation and/or cationic element comprises or preferably consists of Cu and/or Fe. According to particularly preferred embodiments of the present invention, the zeolitic material having an LEV-type framework structure is not first ion-exchanged with an intermediate cation and/or cationic element, in particular $H^+$ and/or $NH_4^+$, before being subject to a further ion-exchange procedure, more preferably before being subject to ion-exchange with one or more of the aforementioned cations and/or cationic elements.

Thus, a further considerable advantage of one or more embodiments of the present invention relies in the fact that the zeolitic material having an LEV-type framework structure may directly be subject to an ion-exchange procedure without first requiring intermediate ion-exchange against cations and/or cationic elements such as $H^+$ and/or $NH_4^+$ as is the case for zeolitic materials containing alkali and/or alkaline earth metals, in particular alkali metals, wherein this applies in particular to sodium and/or potassium contained in said materials. Accordingly, in addition to the aforementioned advantages, it has surprisingly been found that the inventive process also provides a highly efficient synthesis of an ion-exchanged zeolitic material having an LEV-type framework structure, wherein the crystallization product may be directly subject to an ion-exchange procedure with the desired cation and/or cationic element to be loaded thereon, preferably after isolation (3) and/or washing (4) and/or drying and/or calcining (5) of the zeolitic material prior to the ion-exchange procedure.

In general, the preferred isolation (3) and/or washing (4) and/or drying and/or calcining (5) and/or ion-exchange procedures (6) comprised in the inventive process can be conducted the aforementioned sequence or in any conceivably order and combination and may be repeated as often as desired.

Therefore, the inventive process preferably further comprises one or more of the following steps of
  (3) isolating the zeolitic material having an LEV-type framework structure, preferably by filtration, ultrafiltration, diafiltration, centrifugation and/or decantation methods, and/or
  (4) washing the zeolitic material having an LEV-type framework structure, and/or
  (5) drying and/or calcining the zeolitic material having an LEV-type framework structure, and/or
  (6) subjecting the zeolitic material having an LEV-type framework structure to an ion-exchange procedure,
wherein the steps (3) and/or (4) and/or (5) and/or (6) can be conducted in any order, and
wherein one or more of said steps is preferably repeated one or more times.

Preferably, the inventive process comprises at least one step of isolating the zeolitic material crystallized according to step (2), more preferably by filtration thereof. According to said preferred embodiment it is further preferred that after the at least one step of isolating, the zeolitic material is subject to at least one step of drying, wherein more preferably the zeolitic material is subject to at least one step of washing prior to the at least one drying step. In a particularly preferred embodiment, the zeolitic material crystallized according to step (2) is subject to at least one step of isolating, followed by at least one step of washing, followed by at least one step of drying. According to particularly preferred embodiments, pH of the zeolitic material crystallized according to step (2) is additionally adjusted according to preferred embodiments of the inventive process prior to the at least one step of isolating and/or to the at least one step of washing, preferably prior to the at least one step of isolating.

According to an alternative embodiment of the inventive process which is preferred, the zeolitic material crystallized in step (2) is directly subject to at least one step of drying, preferably to spray drying and or spray granulation, preferably without isolating (3) and/or washing (4) and/or drying (5) of the zeolitic material beforehand. Directly subjecting the mixture obtained from step (2) of the inventive process to a spray drying or spray granulation stage has the advantage that isolation and drying is performed in a single stage. Consequently, according to this embodiment of the present invention, an even more preferred process is provided wherein the number of post-synthesis workup steps is further minimized, as a result of which the zeolitic material having an LEV-type framework structure can be obtained from a highly efficient process. According to or alternatively to said preferred embodiment involving a spray drying procedure directly after obtained the zeolitic material in step (2), it is further preferred to apply a step of spray drying to the zeolitic material instead of or directly following any one or more of the steps of isolating (3) and/or washing (4) and/or drying and/or calcining (5) the zeolitic material and/or subjecting the zeolitic material to one or more ion-exchange procedures (6).

Embodiments of the present invention furthermore relate to a zeolitic material having an LEV-type framework structure which is either obtained by the process according to the present invention or by any conceivable process which leads to a zeolitic material having an LEV-type framework structure as obtainable according to the inventive process, wherein according to a preferred embodiment, the zeolitic material is non-ion-exchanged. Within the meaning of embodiments of the present invention, the term "non-ion-exchanged" with respect to the zeolitic material having an LEV-type framework structure indicates that it has not been subject to any type of ion-exchange procedures, and in particular to an ion-exchange procedure involving the exchange of cations and/or cationic elements contained within the zeolitic material as obtained from crystallization in step (2) of the inventive process, wherein the term "non-ion-exchanged" preferably does not include any exchange of the zeolitic material with ft and/or OH⁻ which occurs during pH-adjustment according to preferred embodiments of the present invention.

Therefore, embodiments of the present invention also relate to a zeolitic material having an LEV-type framework structure which is obtainable and/or obtained according to the inventive process, and in particular which is obtainable and/or obtained according to any embodiment or preferred embodiment of the inventive process as outlined in the foregoing, wherein the zeolitic material is preferably non-ion-exchanged.

Furthermore, embodiments of the present invention also relate to a non-ion-exchanged zeolitic material as such having an LEV-type framework structure comprising $YO_2$ and optionally comprising $X_2O_3$, wherein Y is a tetravalent element, and X is a trivalent element, and wherein said zeolitic material contains 3 wt.-% or less of one or more metals M based on 100 wt.-% of X, preferably 3 wt.-% or less, more preferably 1 wt.-% or less, more preferably 0.5 wt.-% or less, more preferably 0.1 wt.-% or less, more preferably 0.05 wt.-% or less, more preferably 0.01 wt.-% or less, more preferably 0.005 wt.-% or less, more preferably 0.001 wt.-% or less, more preferably 0.0005 wt.-% or less, more preferably 0.0001 wt.-% or less of one or more metals M based on 100 wt.-% of X, wherein even more preferably the zeolitic material contains no metal M, wherein M stands for sodium or potassium, preferably for sodium and potassium, more preferably for the group of alkali metals, wherein even more preferably M stands for the group of alkali and alkaline earth metals. According to preferred embodiments of the present invention, said zeolitic material is obtainable and/or obtained according to any one of the embodiments and preferred embodiments of the inventive process, provided that it is a non-ion-exchanged zeolitic material within the meaning of the present invention.

In principle, according to preferred embodiments of the present invention wherein the zeolitic material having an LEV-type framework structure comprises both $YO_2$ and $X_2O_3$, the non-ion-exchanged zeolitic material may display any conceivable Y:X atomic ratio. Thus, by way of example, the Y:X atomic ratio of the zeolitic material may range anywhere from 1 to 200, wherein the zeolitic material preferably displays a Y:X atomic ratio of from 1 to 100, more preferably of from 2 to 50, more preferably of from 5 to 30, more preferably of from 7 to 20, more preferably of from 8 to 15, and even more preferably of from 9 to 14.

According to further preferred embodiments, Y is selected from the group consisting of Si, Sn, Ti, Zr, Ge, and mixtures of two or more thereof, Y preferably being Si. Furthermore, in preferred embodiments comprising $X_2O_3$, it is further preferred that X is selected from the group consisting of Al, B, In, Ga, and mixtures of two or more thereof, X preferably being Al and/or B, and more preferably being Al.

According to preferred embodiments of the present invention, the zeolitic material having an LEV-type framework structure has an X-ray diffraction pattern comprising at least the following reflections:

| Intensity (%) | Diffraction angle 2θ/° [Cu K(alpha 1)] |
|---|---|
| [21-50] | [10.75-11.37] |
| [18-30] | [13.21-13.77] |
| [52-68] | [17.23-17.77] |
| [49-58] | [20.93-21.50] |
| 100 | [21.89-22.43] |
| [34-54] | [28.53-29.09] |
| [36-69] | [32.28-32.78] |
| [9-23] | [51.67-52.23] |
| [6-16] | [55.75-56.36] | wherein 100% relates to the intensity of the maximum peak in the X-ray powder diffraction pattern.

Preferably, the zeolitic material having an LEV-type framework structure has an X-ray diffraction pattern comprises at least the following reflections:

| Intensity (%) | Diffraction angle 2θ/° [Cu K(alpha 1)] |
|---|---|
| [27-45] | [10.87-11.25] |
| [21-27] | [13.32-13.66] |
| [55-65] | [17.34-17.66] |
| [50-56] | [21.04-21.39] |
| 100 | [22.00-22.32] |
| [38-50] | [28.64-28.98] |
| [42-62] | [32.38-32.68] |
| [12-20] | [51.78-52.12] |
| [8-14] | [55.87-56.23] | wherein 100% relates to the intensity of the maximum peak in the X-ray powder diffraction pattern.

According to embodiments of the present invention which are further preferred, at least a portion of the Y atoms in the LEV-type framework is isomorphously substituted by one or more element. In general, Y can be isomorphously substituted by any suitable element, wherein the one or more element is preferably selected from the group consisting of B, Fe, Ti, Sn, Ga, Ge, Zr, V, Nb, Cu, Zn, Li, Be, and mixtures of two or more thereof, more preferably wherein the one or more elements are selected from the group consisting of B, Fe, Ti, Sn, Zr, Cu, and mixtures of two or more thereof, wherein even more preferably the one or more element is Ti and/or B, preferably Ti. According to further embodiments of the present invention which are particularly preferred, the one or more element comprises Cu, wherein it is particularly preferred that the one or more element is Cu. According to yet further embodiments of the present invention which are particularly preferred, the one or more element comprises Fe, wherein it is particularly preferred that the one or more element is Fe.

In general, there is no particular restriction according to the present invention as to the portion of the Y atoms which may be isomorphously substituted in the LEV-type framework of the preferred zeolitic material. According to preferred embodiments, the molar ratio of $YO_2$ to the one or more element ranges from 5 to 100, preferably from 10 to 80, more preferably from 20 to 70, and even more preferably from 25 to 65

Furthermore, there is no particular restriction according to the present invention as to the surface area of the zeolitic material having an LEV-type framework structure. Thus, said material may display a surface area ranging anywhere from 50 to 1,200 m²/g, wherein according to certain embodiments the surface area preferably ranges from 200 to 950 m²/g, more preferably of from 500 to 900 m²/g, more preferably of from 600 to 850 m²/g, and even more preferably of from 650 to 800 m²/g. According to particularly preferred embodiments of the presently claimed, however, the zeolitic material having an LEV-type framework structure, and preferably the calcined zeolitic material, has a BET surface area determined according to DIN 66131 which is comprised in the range of from 650 to 1,100 m²/g, preferably from 750 to 1,050 m²/g, more preferably from 800 to 1,000 m²/g, more preferably from 820 to 900 m²/g, and even more preferably from 840 to 865 m²/g.

Thus, in addition to the aforementioned advantages of the present invention, it has furthermore surprisingly been found that a zeolitic material having an LEV-type framework according to the present invention may be provided, wherein said zeolitic material displays particularly high surface areas compared to known zeolitic materials having an LEV-type framework structure, and in particular compared to zeolitic materials having an LEV-type framework structure which are obtained or obtainable according to a process involving the use of alkali and/or alkaline earth metals, and in particular, compared to those which are obtained or obtainable according to a process involving the use of sodium and/or potassium.

Furthermore, as described above with respect to the inventive process, also the zeolitic material according to the present invention may comprise one or more of any conceivable zeolites having an LEV-type framework structure, provided that said one or more zeolites contain $YO_2$ and optionally contain $X_2O_3$, wherein $YO_2$ and $X_2O_3$ are preferably at least in part contained as a framework element therein, respectively. According to preferred embodiments of the present invention, the zeolitic material comprises one or more zeolites selected from the group consisting of Levyne, LZ-132, NU-3, RU B-1, ZK-20, ZSM-45, RUB-50, and mixtures of two or more thereof, wherein it is particularly preferred that the zeolitic material comprises RUB-50.

Depending on the specific needs of its application, the inventive material can be employed as such, like in the form of a powder, a spray powder or a spray granulate obtained from above-described separation techniques, e.g. decantation, filtration, centrifugation, or spraying.

In many industrial applications, it is often desired on the part of the user not to employ the zeolitic material as powder or sprayed material, i.e. the zeolitic material obtained by the separation of the material from its mother liquor, optionally including washing and drying, and subsequent calcination, but a zeolitic material which is further processed to give moldings. Such moldings are required particularly in many industrial processes, e.g. in many processes wherein the zeolitic material of the present invention is employed as catalyst or adsorbent.

Accordingly, embodiments of the present invention also relate to the zeolitic material of the present invention having an LEV-type framework structure which is comprised in a molding.

In general, the powder or sprayed material can be shaped without any other compounds, e.g. by suitable compacting, to obtain moldings of a desired geometry, e.g. tablets, cylinders, spheres, or the like.

Preferably, the powder or sprayed material is admixed with or coated by a suitable refractory binder. In general, suitable binders are all compounds which impart adhesion and/or cohesion between the zeolitic material particles to be bonded which goes beyond the physisorption which may be present without a binder. Examples of such binders are metal oxides, such as, for example, $SiO_2$, $Al_2O_3$, $TiO_2$, $ZrO_2$ or MgO or clays, or mixtures of two or more of these compounds. Naturally occurring clays which can be employed include the montmorillonite and kaolin family, which families include the subbentonites, and the kaolins commonly known as Dixie, McNamee, Georgia and Florida clays or others in which the main mineral constituent is halloysite, kaolinite, dickite, nacrite, or anauxite. Such clays can be used in the raw state as originally mined or initially subjected to calcination, acid treatment or chemical modification. In addition, the zeolitic material according to the present invention can be composited with a porous matrix material such as silica-alumina, silica-magnesia, silica-zirconia, silica-thoria, silica-beryllia and silica-titania as well as ternary compositions such as silica-alumina-thoria, silica-alumina-zirconia, silica-alumina-magnesia and silica-magnesia-zirconia.

The moldings of embodiments of the present invention may therefore also be provided in the form of extrudates, pellets, tablets or particles of any other suitable shape, for use as a packed bed of particulate catalyst, or as shaped pieces such as plates, saddles, tubes, or the like.

Also preferably, the powder or the sprayed material, optionally after admixing or coating by a suitable refractory binder as described above, is formed into a slurry, for example with water, which is deposited upon a suitable refractory carrier. The slurry may also comprise other compounds such as, e.g., stabilizers, defoamers, promotors, or the like. Typically, the carrier comprises a member, often referred to as a "honeycomb" carrier, comprising one or more refractory bodies having a plurality of fine, parallel gas flow passages extending therethrough. Such carriers are well known in the art and may be made of any suitable material such as cordierite or the like.

In general, the zeolitic material described above can be used as molecular sieve, adsorbent, catalyst, catalyst support or binder thereof. For example, the zeolitic material can be used as molecular sieve to dry gases or liquids, for selective molecular separation, e.g. for the separation of hydrocarbons or amides; as ion exchanger; as chemical carrier; as adsorbent, in particular as adsorbent for the separation of hydrocarbons or amides; or as a catalyst. Most preferably, the zeolitic material according to embodiments of the present invention is used as a catalyst and/or as a catalyst support.

According to a preferred embodiment of the present invention, the zeolitic material of the invention is used in a catalytic process, preferably as a catalyst and/or catalyst support, and more preferably as a catalyst. In general, the zeolitic material of the invention can be used as a catalyst and/or catalyst support in any conceivable catalytic process, wherein processes involving the conversion of at least one organic compound is preferred, more preferably of organic compounds comprising at least one carbon-carbon and/or carbon-oxygen and/or carbon-nitrogen bond, more preferably of organic compounds comprising at least one carbon-carbon and/or carbon-oxygen bond, and even more preferably of organic compounds comprising at least one carbon-carbon bond. In particularly preferred embodiments of the present invention, the zeolitic material is used as a catalyst and/or catalyst support in any one or more of methanol-to-olefin (MTO) reactions, ethylene-to-propylene (ETP) reactions, as well as of the co-reaction of methanol and ethylene (CME).

According to a further embodiment of the present invention, the zeolitic material of the invention is preferably used in a catalytic process involving the conversion of at least one compound comprising at least one nitrogen-oxygen bond. Particularly preferred according to the present invention is the use of the zeolitic material having an LEV-type framework structure as a catalyst and/or catalyst support in a selective catalytic reduction (SCR) process for the selective reduction of nitrogen oxides $NO_x$; for the oxidation of $NH_3$, in particular for the oxidation of $NH_3$ slip in diesel systems; for the decomposition of $N_2O$. The term nitrogen oxides, $NO_x$, as used in the context of the present invention designates the oxides of nitrogen, especially dinitrogen oxide ($N_2O$), nitrogen monoxide (NO), dinitrogen trioxide ($N_2O_3$), nitrogen dioxide ($NO_2$), dinitrogen tetroxide ($N_2O_4$), dinitrogen pentoxide ($N_2O_5$), nitrogen peroxide ($NO_3$). According to particularly preferred embodiments of the present invention, the zeolitic material used in a catalytic process involving the conversion of at least one compound comprising at least one nitrogen-oxygen bond comprises Cu and/or Fe, and more preferably Cu.

Therefore, embodiments of the present invention also relate to a method for selectively reducing nitrogen oxides NO by contacting a stream containing NO with a catalyst containing the zeolitic material having an LEV-type framework structure according to the present invention under suitable reducing conditions; to a method of oxidizing $NH_3$, in particular of oxidizing $NH_3$ slip in diesel systems, by contacting a stream containing $NH_3$ with a catalyst containing the zeolitic material having an LEV-type framework structure according to embodiments of the present invention under suitable oxidizing conditions; to a method of decomposing of $N_2O$ by contacting a stream containing $N_2O$ with a catalyst containing the zeolitic material having an LEV-type framework structure according to embodiments of the present invention under suitable decomposition conditions; to a method of controlling emissions in Advanced Emission Systems such as Homogeneous Charge Compression Ignition (HCCI) engines by contacting an emission stream with a catalyst containing the zeolitic material having an LEV-type framework structure according to embodiments of the present invention under suitable conditions; to a fluid catalytic cracking FCC process wherein the zeolitic material having an LEV-type framework structure according to embodiments of the present invention is employed as additive; to a method of converting an organic compound by contacting said compound with a catalyst containing the zeolitic material having an LEV-type framework structure according to embodiments of the present invention under suitable conversion conditions; to a "stationary source" process wherein a catalyst is employed containing the zeolitic material having an LEV-type framework structure according to embodiments of the present invention.

Accordingly, embodiments of the present invention also relate to a method for selectively reducing nitrogen oxides $NO_x$, wherein a gaseous stream containing nitrogen oxides $NO_x$, preferably also containing ammonia and/or urea, is contacted with the zeolitic material according to the present invention or the zeolitic material obtainable or obtained according to the present invention, preferably in the form of a molded catalyst, still more preferably as a molded catalyst wherein the zeolitic material is deposited on a suitable refractory carrier, still more preferably on a "honeycomb" carrier.

The nitrogen oxides which are reduced using a catalyst containing the zeolitic material according to the present invention or the zeolitic material obtainable of obtained according to the present invention may be obtained by any process, e.g. as a waste gas stream. Among others, waste gas streams as obtained in processes for producing adipic acid, nitric acid, hydroxylamine derivatives, caprolactame, glyoxal, methyl-glyoxal, glyoxylic acid or in processes for burning nitrogenous materials may be mentioned.

Most preferably, the zeolitic material according to embodiments of the present invention or the zeolitic material obtainable of obtained according to embodiments of the present invention is used as a molded catalyst, still more preferably as a molded catalyst wherein the zeolitic material is deposited on a suitable refractory carrier, still more preferably on a "honeycomb" carrier, for the selective reduction of nitrogen oxides $NO_x$, i.e. for selective catalytic reduction of nitrogen oxides. In particular, the selective reduction of nitrogen oxides wherein the zeolitic material according to embodiments of the present invention is employed as catalytically active material is carried out in the presence ammonia or urea. While ammonia is the reducing agent of choice for stationary power plants, urea is the reducing agent of choice for mobile SCR systems. Typically, the SCR system is integrated in the engine and vehicle design and, also typically, contains the following main components: SCR catalyst containing the zeolitic material according to embodiments of the present invention; a urea storage tank; a urea pump; a urea dosing system; a urea injector/nozzle; and a respective control unit.

Especially preferred is the use of a catalyst containing the zeolitic material according to embodiments of the present invention or the zeolitic material obtainable or obtained according to the inventive process for removal of nitrogen oxides $NO_x$ from exhaust gases of internal combustion engines, in particular diesel engines, which operate at combustion conditions with air in excess of that required for stoichiometric combustion, i.e. in a lean operation mode.

Therefore, embodiments of the present invention also relate to a method for removing nitrogen oxides $NO_x$ from exhaust gases of internal combustion engines, in particular diesel engines, which operate at combustion conditions with air in excess of that required for stoichiometric combustion, i.e., at lean conditions, wherein a catalyst containing the zeolitic material according to embodiments of the present invention or the zeolitic material obtainable or obtained according to embodiments of the present invention is employed as catalytically active material.

Embodiments of the present invention therefore relate to the use of the zeolitic material of the invention, in particular in the field of catalysis and/or in the treatment of exhaust gas, wherein said exhaust gas treatment comprises industrial and automotive exhaust gas treatment. In these and other applications, the zeolitic material of the present invention can by way of example be used as a molecular sieve, catalyst, and/or catalyst support.

Furthermore, it is preferred according to the present invention that the zeolitic material is used as a molecular trap for organic compounds. In general, any type of organic compound may be trapped in the zeolitic material, wherein it is preferred that the compound is reversibly trapped, such that it may be later released from the zeolitic material, preferably wherein the organic compound is released—preferably without conversion thereof—by an increase in temperature and/or a decrease in pressure. Furthermore, it is preferred that the zeolitic material is used to trap organic compounds of which the dimensions allow them to penetrate the microporous system of the molecular structure. According to yet further embodiments of the present invention, it is preferred that the trapped compounds are released under at least partial conversion thereof to a chemical derivative and/or to a decomposition product thereof, preferably to a thermal decomposition product thereof.

Therefore, embodiments of the present invention also relate to the use of a zeolitic material according to embodiments and preferred embodiments of the present invention as a molecular sieve, catalyst, catalyst support, and/or as an adsorbent, wherein the zeolitic material is preferably used as a molecular trap for chemical compounds, as a catalyst and/or as a catalyst support.

When preparing specific catalytic compositions or compositions for different purposes, it is also conceivable to blend the zeolitic material according to embodiments of the present invention having an LEV-type framework structure with at least one other catalytically active material or a material being active with respect to the intended purpose. It is also possible to blend at least two different inventive materials which may differ in the Y:X ratio, preferably in the Si:Al ratio, and/or in the presence or absence of one or more further metals such as one or more transition metals and/or in the specific amounts of a further metal such as a transition metal, wherein according to particularly preferred embodiments, the one or more transition metal comprises Cu and/or Fe, more preferably Cu. It is also possible to blend at least two different inventive materials with at least one other catalytically active material or a material being active with respect to the intended purpose.

As mentioned in the foregoing with respect to preferred embodiments, the zeolitic material having an LEV-type framework structure may be disposed on a substrate. In general, the substrate may be any of those materials typically used for preparing catalysts, and preferably comprises a ceramic or metal honeycomb structure. Any suitable substrate may be employed, such as a monolithic substrate of the type having fine, parallel gas flow passages extending therethrough from an inlet or an outlet face of the substrate, such that passages are open to fluid flow therethrough (referred to as honeycomb flow through substrates). The passages, which are essentially straight paths from their fluid inlet to their fluid outlet, are defined by walls on which the zeolitic material is disposed as a washcoat so that the gases flowing through the passages contact the catalytic material. The flow passages of the monolithic substrate are thin-walled channels, which can be of any suitable cross-sectional shape and size such as trapezoidal, rectangular, square, sinusoidal, hexagonal, oval, circular, etc. Such structures may contain from about 60 to about 400 or more gas inlet openings (i.e., cells) per square inch (2.54 cm×2.54 cm) of cross section.

The substrate can also be a wall-flow filter substrate, where the channels are alternately blocked, allowing a gaseous stream entering the channels from one direction (inlet direction), to flow through the channel walls and exit from the channels from the other direction (outlet direction). The catalyst composition can be coated on the flow through or wall-flow filter. If a wall flow substrate is utilized, the resulting system will be able to remove particulate matter along with gaseous pollutants. The wall-flow filter substrate can be made from materials commonly known in the art, such as cordierite, aluminum titanate or silicon carbide. It will be understood that the loading of the catalytic composition on a wall flow substrate will depend on substrate properties such as porosity and wall thickness, and typically will be lower than loading on a flow through substrate.

The ceramic substrate may be made of any suitable refractory material, e.g., cordierite, cordierite-alumina, silicon nitride, zircon mullite, spodumene, alumina-silica magnesia, zircon silicate, sillimanite, a magnesium silicate, zircon, petalite, alpha-alumina, an aluminosilicate, and the like.

The substrates useful for embodiments of the present invention wherein the inventive zeolitic material is used as a catalyst may also be metallic in nature and be composed of one or more metals or metal alloys. The metallic substrates may be employed in various shapes such as corrugated sheet or monolithic form. Suitable metallic supports include the heat resistant metals and metal alloys such as titanium and stainless steel as well as other alloys in which iron is a substantial or major component. Such alloys may contain one or more of nickel, chromium and/or aluminum, and the total amount of these metals may advantageously comprise at least 15 wt. % of the alloy, e.g., 10-25 wt. % of chromium, 3-8 wt. % of aluminum and up to 20 wt. % of nickel. The alloys may also contain small or trace amounts of one or more other metals such as manganese, copper, vanadium, titanium, and the like. The surface or the metal substrates may be oxidized at high temperatures, e.g., 1000° C. and higher, to improve the resistance to corrosion of the alloys by forming an oxide layer on the surfaces of the substrates. Such high temperature-induced oxidation may enhance the adherence of the refractory metal oxide support and catalytically promoting metal components to the substrate.

In alternative embodiments, the zeolitic material according to the present invention having an LEV-type framework structure may be deposited on an open cell foam substrate. Such substrates are well known in the art, and are typically formed of refractory ceramic or metallic materials.

The powder X-ray diffraction patterns displayed in the figures were recorded on a Siemens D-5000 with monochromatic Cu K alpha-1 radiation, a capillary sample holder being used in order to avoid a preferred orientation. The diffraction data were collected using a position-sensitive detector from Braun, in the range from 8 to 96° (2 theta) and with a step width of 0.0678°. Indexing of the powder diagram was effected using the program Treor90, implemented in powder-X (Treor90 is a public domain program which is freely accessible via the URL http://www.ch.iucr.org/sincris-top/logiciel/). In the figure, the angle 2 theta in ° is shown along the abscissa and the intensities are plotted along the ordinate.

EXAMPLES

Example 1

13.35 kg of an aqueous diethyldimethylammonium hydroxide solution (20 wt.-%) and 252.3 g of aluminum hydroxide were placed in a plastic receptacle and the mixture was stirred for 10 min to afford a slightly cloudy solution. 2.7 kg of fumed silica (Aerosil 200) were then added in portions and the resulting mixture stirred for 1 h to afford a milky suspension.

The mixture was then transferred to an autoclave and 6.6 kg of water was distilled off at 105° C., after which the resulting mixture was then crystallized under autogenous pressure at 150° C. for 120 hours (11 days). After having let the reaction mixture cool to room temperature, the reaction product consisted of a white suspension with a pH of 12.6. A small portion of the white suspension was placed in a porcelain drying dish and dried for 16 h at 100° C. to afford 35.5 g of a white powder.

Elemental Analysis:
Si: 32 g/100 g
Al: 2.3 g/100 g

Therefore, according to elemental analysis, the Si:Al molar ratio of the product is approximately 13.4.

FIG. 1 shows the XRD of the crystalline product obtained from the synthesis of Example 1. In particular, the XRD reflection pattern of the microcrystalline product reveals an LEV-type zeolite framework structure.

Example 2

1 kg of the white suspension obtained from hydrothermal synthesis in Example 1 was separated from the crystallization product and then treated with 1.256 kg of aqueous $HNO_3$ (5 wt.-%) to afford a suspension with a pH of 10.02, after which 47.61 g of concentrated aqueous $HNO_3$ (65 wt.-%) were added to afford a highly viscous suspension having a pH of 8.1. A further 477.7 g of the white suspension obtained from Example 1 were then added to the acidified mixture, to afford a final mixture having a pH of 8.63. Said mixture was filtered off and washed with 5.7 kg of distilled water wherein the conductivity of the washing was thus lowered to less than 200 $\mu S/cm^3$. The resulting wet cake was then dried at 120° C. for 16 h to afford 394.2 g of a white powder.

Elemental Analysis:
Si: 33 g/100 g
Al: 2.4 g/100 g

Therefore, according to elemental analysis, the Si:Al molar ratio of the product is approximately 13.3.

Figure 2:
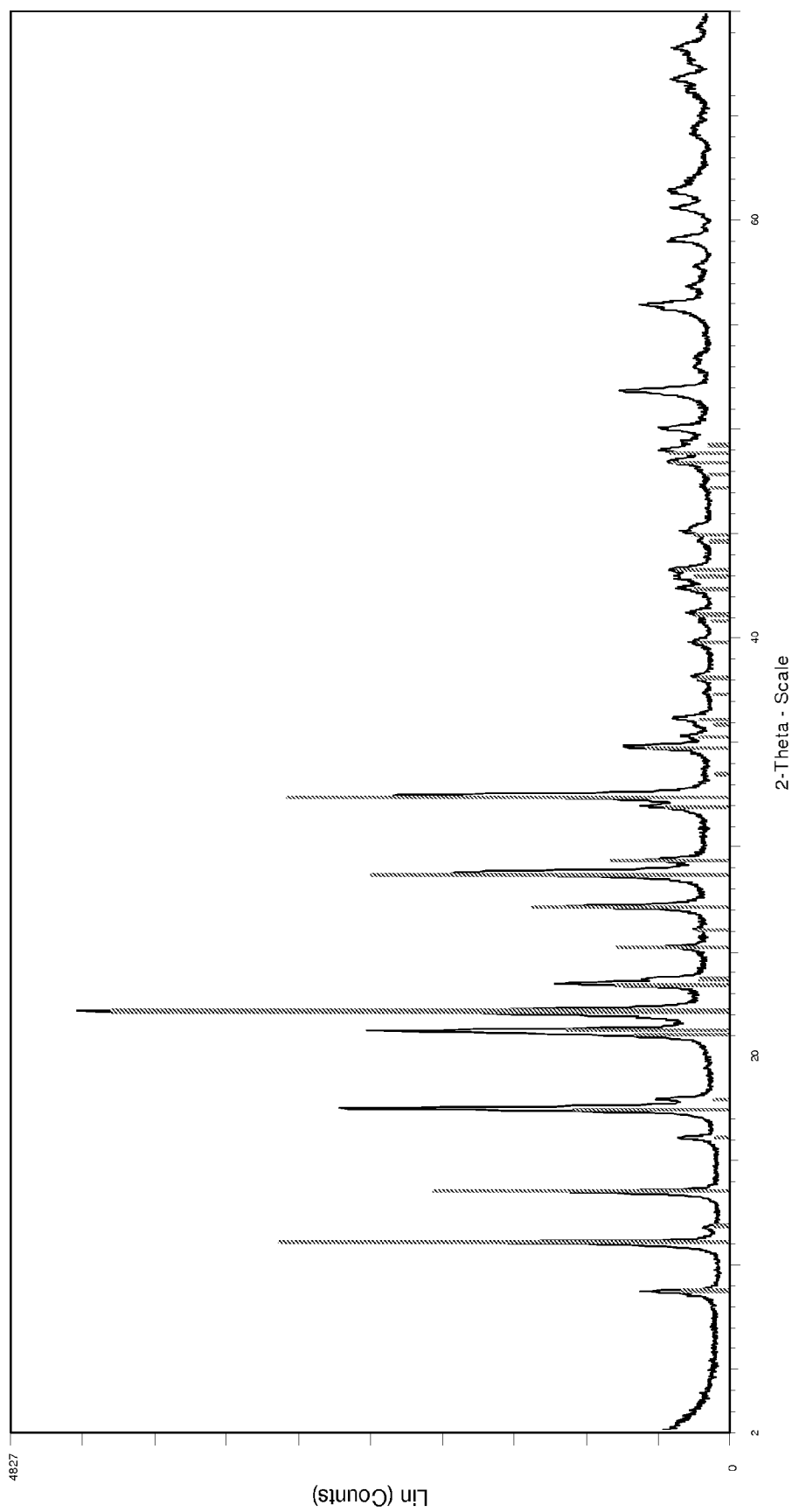

FIG. 2 shows the XRD of the crystalline product obtained from the synthesis of Example 2. In particular, the line pattern of a typical LEV-type framework is included in the XRD reflection pattern of the microcrystalline product, thus confirming the presence of an LEV-type zeolite framework structure.

Example 3

8.038 kg of the white suspension from the hydrothermal synthesis in Example 1 were treated with 5.14 kg of aqueous $HNO_3$ (10 wt.-%) to afford a highly viscous suspension with a pH of 8.2. The resulting suspension was filtered off and washed with 40 l of distilled water wherein the conductivity of the washing was thus lowered to less than 160 $\mu S/cm^3$. The resulting wet cake was then dried at 120° C. for 16 h to afford 2.37 kg of a white powder.

Elemental Analysis:
Si: 34 g/100 g
Al: 2.5 g/100 g

Therefore, according to elemental analysis, the Si:Al molar ratio of the product is approximately 13.1.

Figure 3:
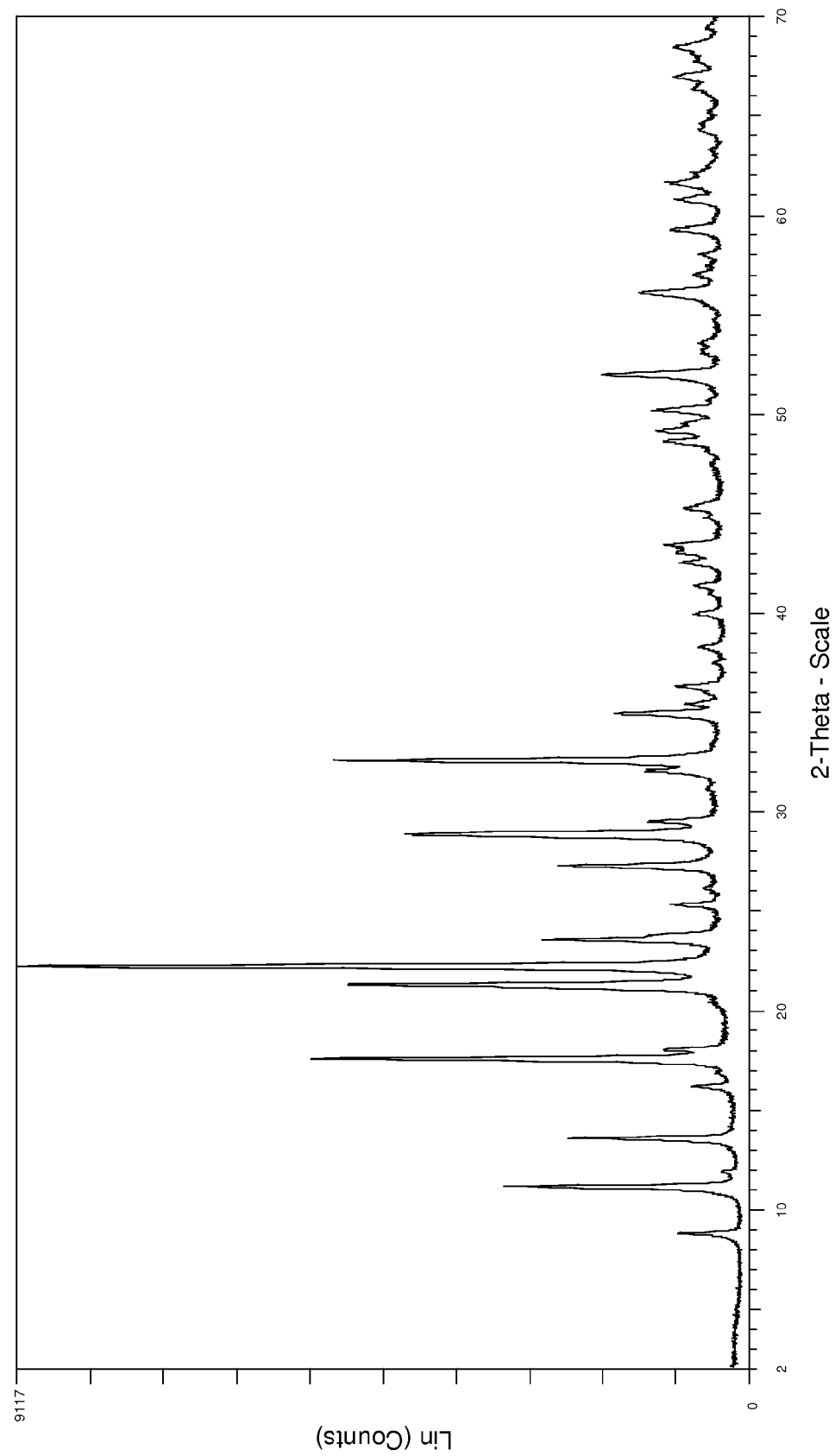

FIG. 3 shows the XRD of the crystalline product obtained from the synthesis of Example 3. In particular, the XRD reflection pattern of the microcrystalline product reveals an LEV-type zeolite framework structure.

Example 4

1.5 g of an aqueous diethyldimethylammonium hydroxide solution (40 wt.-%) and 78 mg of aluminum hydroxide were mixed together and stirred for 20 min, after which 0.6 g of fumed silica (Cab-O-Sil M5) was added. The mixture was then transferred to a 20 ml Teflon lined autoclave in which it was crystallized under autogenous pressure at 150° C. for 3 d, during which the reaction vessel was tumbled at 20 rpm. After having let the reaction mixture cool to room temperature, the reaction product was centrifuged at 4 krpm for 50 min, and the white solid repeatedly elutriated with distilled water. The washed solid was then isolated by centrifugation and dried at 100° C. for 16 h, after which the resulting white powder was calcined at 600° C. for 10 h.

The surface area of the crystalline product of Example 4 was investigated by nitrogen absorption (cf. DIN 66131), wherein the evaluation of the data afforded a BET surface area of 603 m²/g.

The resulting product was analyzed by inductively coupled plasma mass spectrometry (ICP-MS), thus affording in Si:Al ratio of 10.

Investigation of the product of Example 4 by $^{27}$Al MAS NMR reveals two signals at 55.9 ppm and −1.31 ppm, respectively. In particular, the signal at 55.9 ppm results from tetrahedrally coordinated aluminum, whereas the signal measured at −1.31 ppm originates from higher-coordinated aluminum, and in particular from aluminum in a five-coordinate and/or in an octahedral coordination environment.

Example 5

The procedure of Example 4 was repeated, wherein the mixture was crystallized for 7 d.

The surface area of the crystalline product of Example 5 was investigated by nitrogen absorption (cf. DIN 66135), wherein the evaluation of the data afforded a BET surface area of 860 m²/g.

The crystalline product of Example 5 was analyzed by inductively coupled plasma mass spectrometry (ICP-MS), thus affording in Si:Al ratio of 10.

Example 6

The procedure of Example 4 was repeated, wherein the mixture was crystallized for 13 d.

The surface area of the crystalline product of Example 6 was investigated by nitrogen absorption (cf. DIN 66131), wherein the evaluation of the data afforded a BET surface area of 846 m²/g.

The crystalline product of Example 6 was analyzed by inductively coupled plasma mass spectrometry (ICP-MS), thus affording in Si:Al ratio of 10.

Comparative Example 1

0.2 g of sodium hydroxide were placed in a plastic receptacle and dissolved under stirring in 10.9 g of water, after which 140.8 g of an aqueous diethyldimethylammonium hydroxide solution (20.62 wt.-%) were then added to the sodium hydroxide solution. 1.4 g of sodium aluminate and 1 g of chabazite seed crystals were then added to the solution. 26.6 g of fumed silica (Aerosil 200) were then added in portions and the resulting mixture was stirred for 1 h.

The mixture was then transferred to an autoclave and crystallized under autogenous pressure at 130° C. for 29.5 days. After having let the reaction mixture cool to room temperature, the resulting white suspension was isolated from the reaction mixture by centrifugation, and the white solid repeatedly elutriated with distilled water until pH neutrality was achieved. The resulting solid was then dried at 120° C. for 16 h and subsequently calcined at 550° C. for 4 hours thus affording 11.4 g of a white powder.

Electron Probe Micro Analysis of the crystalline product of Comparative Example 1 via Energy Dispersive X-Ray Spectroscopy (EDXS) afforded an Si:Al molar ratio of about 12.4.

The surface area of the crystalline product of Comparative Example 1 was 5 investigated by nitrogen absorption (cf. DIN 66131), wherein the evaluation of the data afforded a BET surface area of 635 m²/g.

Thus, compared with the surface area of the products obtained in Examples 5 and 6, it is apparent that according to the inventive process it is possible to obtain zeolitic materials displaying a considerably increased surface area. In particular, it has surprisingly been found that the inventive process may lead to zeolitic material having an LEV-type framework structure which display surface areas that may not be achieved according to the known synthetic procedures, and in particular in a one-pot synthetic methodology.

Comparative Example 2

12.92 kg of an aqueous diethyldimethylammonium hydroxide solution (20.62 wt.-%) were placed in a plastic receptacle and 90.1 g of NaOH were then dissolved therein under stirring. 351.9 g of aluminum hydroxide were then added, and the resulting solution was then stirred for 10 min, to afford a slightly cloudy solution. 2.74 kg of fumed silica (Aerosil 200) were then added in portions and the resulting mixture stirred for 1 h, after which 135.3 g of the crystalline product from Example 3 were added as seed crystals to the mixture which was stirred a further 1 h to afford a milky suspension.

The mixture was then transferred to an autoclave and 6.2 kg of water was distilled off at 105° C., after which the resulting mixture was then crystallized under autogenous pressure at 150° C. for 168 hours (7 days). After having let the reaction mixture cool to room temperature, the reaction product consisted of a solid crust in a top portion, under which a white suspension was contained. A portion of the white suspension displaying a pH of 12.35 was isolated from the reaction mixture, centrifuged, and the white solid washed with distilled water until a conductivity of the washing water of less than 200 µS/cm³ was achieved. The resulting wet cake was then dried at 120° C. for 16 h to afford 1.03 kg of a white powder.

Electron Probe Micro Analysis of the crystalline product of Comparative Example 2 via Energy Dispersive X-Ray Spectroscopy (EDXS) afforded an Si:Al molar ratio of about 11.4.

Comparative Example 3

5.7 kg of the white suspension obtained from hydrothermal synthesis in Comparative Example 2 was isolated from the reaction mixture, and then treated with 3 kg of aqueous HNO₃ (10 wt.-%) to afford a pH of 9.3. The solid was then filtered off and washed with 59 l of distilled water until a conductivity of the washing water of less than 200 µS/cm³ was achieved. The resulting wet cake was dried at 120° C. for 16 h thus affording 1.56 kg of a white powder.

Electron Probe Micro Analysis of the crystalline product of Comparative Example 2 via Energy Dispersive X-Ray Spectroscopy (EDXS) afforded an Si:Al molar ratio of about 13.

Accordingly, upon comparing the results of Examples 1-3 of the present invention which are conducted in the absence of alkali and alkaline earth metals with those of the Comparative Examples 1 and 2 which employ sodium, it has quite unexpectedly found that the effect of acidifying the crystallized products leads to opposite effects with respect to the Si:Al ratios thereof. More specifically, upon comparing the Si:Al ratio of the crystalline product obtained from Comparative Example 1 with that of the product obtained from Comparative Example 2 which includes an acidification step, it is observed that acidification leads to a net increase in the Si:Al molar ratio of the product in Comparative Example 2. This actually corresponds to the behavior which is often observed upon acidification—also referred to as acid leaching—of aluminosilicates, wherein the Si:Al molar ratio is increased, indicating a dealumination of the aluminosilicate material.

Regarding the zeolitic materials having an LEV-type framework structure obtained according to the inventive process, however, it has quite unexpectedly been found that an acidification of the crystalline product actually leads to the opposite effect, i.e. to a slight decrease in the Si:Al molar ratio. This highly unexpected finding not only further distinguishes the inventive process, but also clearly underlines the unique constitution and properties of the zeolitic material of the present invention which is obtainable according to the inventive process.

The invention claimed is:

1. A process for the production of a zeolitic material having an LEV-type framework structure comprising $YO_2$ and optionally comprising $X_2O_3$, wherein said process comprises:
   (1) preparing a mixture comprising one or more sources for $YO_2$, one or more solvents, one or more tetraalkylammonium compounds, and optionally comprising seed crystals; and
   (2) crystallizing the mixture obtained in step (1);
   wherein Y is a tetravalent element, and X is a trivalent element, and
   wherein the mixture obtained in step (1) and to be crystallized in step (2) contains less than 0.01 wt. % of sodium and potassium based on 100 wt % of $YO_2$.

2. The process of claim 1, wherein the molar ratio of the total amount of the one or more solvents to $YO_2$ of the mixture obtained in step (1) is 50 or less.

3. The process of claim 1, wherein the one or more solvents comprise one or more polar solvents.

4. The process of claim 1, wherein the molar ratio of the total amount of the one or more tetraalkylammonium compounds to $YO_2$ of the mixture obtained in step (1) ranges from 0.01 to 2.

5. The process of claim 1, wherein Y is selected from the group consisting of Si, Sn, Ti, Zr, Ge, and mixtures of two or more thereof.

6. The process of claim 1, wherein X is selected from the group consisting of Al, B, In, Ga, and mixtures of two or more thereof.

7. The process of claim 1, wherein the one or more sources for $YO_2$ comprises silica.

8. The process of claim 1, wherein the mixture in step (1) further comprises one or more sources for $X_2O_3$.

9. The process of claim 8, wherein the one or more sources for $X_2O_3$ comprises one or more aluminum compounds.

10. The process of claim 8, wherein the $YO_2:X_2O_3$ molar ratio of the mixture obtained in step (1) ranges from 2 to 200.

11. The process of claim 1, wherein the mixture according to step (1) further comprises one or more sources for $OH^-$.

12. The process of claim 11, wherein the $OH^-:YO_2$ molar ratio of the mixture obtained in step (1) ranges from 0.01 to 5.

13. The process of claim 1, wherein the mixture according to step (1) further comprises one or more sources of one or more elements suitable for isomorphous substitution of at least a portion of the Y atoms and/or of the X atoms in the LEV-type framework structure.

14. The process of claim 13, wherein the molar ratio of $YO_2$ to the total amount of the one or more elements suitable for isomorphous substitution of at least a portion of the Y atoms and/or of the X atoms in the LEV-type framework structure ranges from 3 to 300.

15. The process of claim 1, wherein the mixture in step (1) further comprises one or more sources for $X_2O_3$, and wherein the molar ratio of $YO_2$ to $X_2O_3$ to the total amount of the one or more tetraalkylammonium compounds of the mixture obtained in step (1) ranges from 1:(0.005-1):(0.05-10).

16. The process of claim 1, wherein the crystallization in step (2) involves heating of the mixture.

17. The process of claim 1, wherein the crystallization in step (2) is conducted under solvothermal conditions.

18. The process of claim 16, wherein the crystallization in step (2) involves heating of the mixture for at least 0.1 d.

19. The process of claim 1, wherein the crystallization in step (2) involves agitating the mixture.

20. The process of claim 1, further comprising one or more of the following:
   (3) isolating the zeolitic material having an LEV-type framework structure, and/or
   (4) washing the zeolitic material having an LEV-type framework structure, and/or
   (5) drying and/or calcining the zeolitic material having an LEV-type framework structure, and/or
   (6) subjecting the zeolitic material having an LEV-type framework structure to an ion-exchange procedure,
   wherein the steps (3) and/or (4) and/or (5) and/or (6) can be conducted in any order.

21. The process of claim 20, wherein the calcination in step (5) is conducted at a temperature in the range of from 300 to 900° C.

22. The process of claim 20, wherein after step (2) and prior to step (3) the pH of the crystallization product is adjusted to a pH in the range of from 5 to 12.

23. The process of claim 20, wherein in step (6) the zeolitic material having an LEV-type framework is ion-exchanged with at least one cation and/or cationic element.

24. The process of claim 1, wherein the zeolitic material having an LEV-type framework structure formed in step (2) comprises one or more zeolites selected from the group consisting of Levyne, LZ-132, NU-3, RUB-1, ZK-20, ZSM-45, RUB-50, and mixtures of two or more thereof.

25. The process of claim 1, wherein the seed crystals at least partially comprise zeolitic material not having an LEV-type framework structure.

26. The process of claim 25, wherein the zeolitic material not having an LEV-type framework structure contained in the seed crystals comprises zeolitic material having a CHA-type framework structure.

27. The process of claim 1, wherein the seed crystals at least partially comprise zeolitic material having an LEV-type framework structure.

28. The process of claim 27, wherein the zeolitic material having an LEV-type framework structure contained in the seed crystals comprises one or more zeolites selected from the group consisting of Levyne, LZ-132, NU-3, RUB-1, ZK-20, ZSM-45, RUB-50.

29. The process of claim 1, wherein the amount of seed crystals in the mixture according to step (1) ranges from 0.01 to 30 wt.-% based on 100 wt.-% of $YO_2$ in the at least one source for $YO_2$.

30. The process of claim 1, wherein the mixture according to step (1) contains 5 wt.-% or less of seed crystals based on 100 wt.-% of $YO_2$.

31. A zeolitic material having an LEV-type framework structure obtainable according to the process of claim 1.

32. A non-ion-exchanged zeolitic material, said zeolitic material having an LEV-type framework structure comprising $YO_2$ and comprising $X_2O_3$, wherein Y is a tetravalent element, and X is a trivalent element, wherein the non-ion-exchanged zeolitic material contains less than 0.1 wt. % of sodium and potassium based on 100 wt. % of X, and wherein the BET surface area of the calcined zeolitic material determined according to DIN 66131 ranges from 650 to 1,100 $m^2/g$.

33. The zeolitic material of claim 32, wherein the LEV-type framework structure comprises $X_2O_3$, and wherein the zeolitic material displays an Y:X atomic ratio of from 1 to 200.

34. The zeolitic material of claim 32, wherein Y is selected from the group consisting of Si, Sn, Ti, Zr, Ge, and mixtures of two or more thereof.

35. The zeolitic material of claim 32, wherein X is selected from the group consisting of Al, B, In, Ga, and mixtures of two or more thereof.

36. The zeolitic material of claim 32, said material having an X-ray diffraction pattern comprising at least the following reflections:

| Intensity (%) | Diffraction angle 2θ/° [Cu K(alpha 1)] |
|---|---|
| [21-50] | [10.75-11.37] |
| [18-30] | [13.21-13.77] |
| [52-68] | [17.23-17.77] |
| [49-58] | [20.93-21.50] |
| 100 | [21.89-22.43] |
| [34-54] | [28.53-29.09] |
| [36-69] | [32.28-32.78] |
| [9-23] | [51.67-52.23] |
| [6-16] | [55.75-56.36] | wherein 100% relates to the intensity of the maximum peak in the X-ray powder diffraction pattern.

37. The zeolitic material of claim 32, wherein at least a portion of the Y atoms and/or of the X atoms in the LEV-type framework structure is isomorphously substituted by one or more elements.

38. The zeolitic material of claim 37, wherein the molar ratio of $YO_2$ to the total amount of the one or more elements by which the LEV-type framework structure is isomorphously substituted ranges from 5 to 100.

39. The zeolitic material of claim 32, wherein said material comprises one or more zeolites selected from the group consisting of Levyne, LZ-132, NU-3, RUB-1, ZK-20, ZSM-45, RUB-50.

40. A method of catalyzing a chemical reaction comprising the step of contacting one or more chemical compounds with the zeolitic material according to claim 32.

* * * * *